United States Patent
Kim et al.

(10) Patent No.: US 9,623,119 B1
(45) Date of Patent: Apr. 18, 2017

(54) ACCENTUATING SEARCH RESULTS

(75) Inventors: Hyung-Jin Kim, Sunnyvale, CA (US);
Leonard Wei, Sunnyvale, CA (US)

(73) Assignee: Google Inc., Mountain View, CA (US)

( * ) Notice: Subject to any disclaimer, the term of this patent is extended or adjusted under 35 U.S.C. 154(b) by 312 days.

(21) Appl. No.: 12/825,461

(22) Filed: Jun. 29, 2010

(51) Int. Cl.
*A61K 48/00* (2006.01)
*G06F 17/30* (2006.01)

(52) U.S. Cl.
CPC .......... *A61K 48/00* (2013.01); *G06F 17/3053* (2013.01)

(58) Field of Classification Search
CPC .............. G06F 17/30; G06F 17/30864; G06F 17/30011; G06F 17/3053
USPC ........... 707/706, 709, 723; 11/706, 709, 723
See application file for complete search history.

(56) References Cited

U.S. PATENT DOCUMENTS

| | | | |
|---|---|---|---|
| 5,265,065 A | 11/1993 | Turtle | |
| 5,488,725 A | 1/1996 | Turtle | |
| 5,696,962 A | 12/1997 | Kupiec | |
| 5,920,854 A | 7/1999 | Kirsch et al. | |
| 5,963,940 A | 10/1999 | Liddy et al. | |
| 6,006,222 A | 12/1999 | Culliss | |
| 6,006,225 A | 12/1999 | Bowman et al. | |
| 6,014,665 A | 1/2000 | Culliss | |
| 6,026,388 A | 2/2000 | Liddy et al. | |
| 6,067,565 A | 5/2000 | Horvitz | |
| 6,076,051 A | 6/2000 | Messerly et al. | |
| 6,078,916 A | 6/2000 | Culliss | |
| 6,078,917 A | 6/2000 | Paulsen et al. | |
| 6,088,692 A | 7/2000 | Driscoll | |
| 6,134,532 A | 10/2000 | Lazarus et al. | |
| 6,182,066 B1 | 1/2001 | Marques et al. | |
| 6,182,068 B1 | 1/2001 | Culliss | |
| 6,185,559 B1 | 2/2001 | Brin et al. | |
| 6,249,252 B1 | 6/2001 | Dupray | |

(Continued)

FOREIGN PATENT DOCUMENTS

WO  WO 00/77689  12/2000
WO  WO 01/16807  3/2001

(Continued)

OTHER PUBLICATIONS

Agichtein, et al; *Improving Web Search Ranking by Incorporating User Behavior Information*; Aug. 2006; Proceedings of the Twenty-Ninth Annual International ACM SIGIR Conference on Research and Development in Information Retrieval, p. 19-26.

(Continued)

*Primary Examiner* — Mariela Reyes
*Assistant Examiner* — Soheila Davanlou
(74) *Attorney, Agent, or Firm* — Fish & Richardson P.C.

(57) ABSTRACT

Methods, systems, and apparatus, including computer programs encoded on a computer storage medium, for improving search results. In one aspect, a method includes receiving documents responsive to a query, each document having an associated score indicative of the document's relevance to the query. The method includes determining, for a plurality of the associated scores, a distribution of the scores along a dimension that measures trustworthiness of the scores. The method also includes reducing each of one or more of the plurality of associated scores by an amount determined based on the score's respective trustworthiness and properties of the distribution, and ranking the documents to account for the reduced scores.

32 Claims, 11 Drawing Sheets

(56) References Cited

U.S. PATENT DOCUMENTS

| | | |
|---|---|---|
| 6,269,368 B1 | 7/2001 | Diamond |
| 6,285,999 B1 | 9/2001 | Page |
| 6,321,228 B1 | 11/2001 | Crandall et al. |
| 6,327,590 B1 | 12/2001 | Chidlovskii et al. |
| 6,334,132 B1* | 12/2001 | Weeks .............. G06F 17/30719 707/723 |
| 6,341,283 B1 | 1/2002 | Yamakawa et al. |
| 6,353,849 B1 | 3/2002 | Linsk |
| 6,363,378 B1 | 3/2002 | Conklin et al. |
| 6,370,526 B1 | 4/2002 | Agrawal et al. |
| 6,421,675 B1 | 7/2002 | Ryan et al. |
| 6,473,752 B1 | 10/2002 | Fleming, III |
| 6,480,843 B2 | 11/2002 | Li |
| 6,490,575 B1 | 12/2002 | Berstis |
| 6,526,440 B1 | 2/2003 | Bharat |
| 6,529,903 B2 | 3/2003 | Smith et al. |
| 6,539,377 B1 | 3/2003 | Culliss |
| 6,560,590 B1 | 5/2003 | Shwe et al. |
| 6,567,103 B1* | 5/2003 | Chaudhry .................... 715/738 |
| 6,587,848 B1 | 7/2003 | Aggarwal et al. |
| 6,615,209 B1 | 9/2003 | Gomes |
| 6,623,529 B1 | 9/2003 | Lakritz |
| 6,640,218 B1 | 10/2003 | Golding et al. |
| 6,658,423 B1 | 12/2003 | Pugh et al. |
| 6,671,681 B1 | 12/2003 | Emens et al. |
| 6,678,681 B1 | 1/2004 | Brin et al. |
| 6,701,309 B1 | 3/2004 | Beeferman et al. |
| 6,725,259 B1 | 4/2004 | Bharat |
| 6,738,764 B2 | 5/2004 | Mao et al. |
| 6,754,873 B1 | 6/2004 | Law et al. |
| 6,792,416 B2 | 9/2004 | Soetarman et al. |
| 6,795,820 B2 | 9/2004 | Barnett |
| 6,816,850 B2 | 11/2004 | Culliss |
| 6,853,993 B2 | 2/2005 | Ortega et al. |
| 6,873,982 B1 | 3/2005 | Bates et al. |
| 6,877,002 B2 | 4/2005 | Prince |
| 6,882,999 B2 | 4/2005 | Cohen et al. |
| 6,901,402 B1 | 5/2005 | Corston-Oliver et al. |
| 6,912,505 B2 | 6/2005 | Linden et al. |
| 6,944,611 B2 | 9/2005 | Flank et al. |
| 6,944,612 B2 | 9/2005 | Roustant et al. |
| 6,954,750 B2 | 10/2005 | Bradford |
| 6,963,867 B2 | 11/2005 | Ford et al. |
| 6,990,453 B2 | 1/2006 | Wang et al. |
| 7,016,939 B1 | 3/2006 | Rothwell et al. |
| 7,028,027 B1 | 4/2006 | Zha et al. |
| 7,072,886 B2 | 7/2006 | Salmenkaita et al. |
| 7,085,761 B2 | 8/2006 | Shibata |
| 7,113,939 B2 | 9/2006 | Chou et al. |
| 7,117,206 B1 | 10/2006 | Bharat et al. |
| 7,136,849 B2 | 11/2006 | Patrick |
| 7,146,361 B1 | 12/2006 | Broder et al. |
| 7,222,127 B1 | 5/2007 | Bem et al. |
| 7,231,399 B1 | 6/2007 | Bem et al. |
| 7,243,102 B1 | 7/2007 | Naam et al. |
| 7,249,126 B1 | 7/2007 | Ginsburg et al. |
| 7,266,765 B2 | 9/2007 | Golovchinsky et al. |
| 7,293,016 B1 | 11/2007 | Shakib et al. |
| 7,379,951 B2 | 5/2008 | Chkodrov et al. |
| 7,382,358 B2 | 6/2008 | Kushler et al. |
| 7,395,222 B1 | 7/2008 | Sotos |
| 7,426,507 B1 | 9/2008 | Patterson |
| 7,451,487 B2 | 11/2008 | Oliver et al. |
| 7,499,919 B2 | 3/2009 | Meyerson et al. |
| 7,505,964 B2 | 3/2009 | Tong et al. |
| 7,516,146 B2 | 4/2009 | Robertson et al. |
| 7,526,470 B1 | 4/2009 | Karnawat et al. |
| 7,533,092 B2 | 5/2009 | Berkhin et al. |
| 7,533,130 B2 | 5/2009 | Narayana et al. |
| 7,552,112 B2 | 6/2009 | Jhala et al. |
| 7,565,363 B2 | 7/2009 | Anwar |
| 7,565,367 B2 | 7/2009 | Barrett et al. |
| 7,566,363 B2 | 7/2009 | Starling et al. |
| 7,574,530 B2 | 8/2009 | Wang et al. |
| 7,584,181 B2 | 9/2009 | Zeng et al. |
| 7,603,350 B1* | 10/2009 | Guha |
| 7,610,282 B1 | 10/2009 | Datar et al. |
| 7,636,714 B1 | 12/2009 | Lamping et al. |
| 7,657,626 B1 | 2/2010 | Zwicky |
| 7,676,507 B2 | 3/2010 | Maim |
| 7,680,775 B2 | 3/2010 | Levin et al. |
| 7,693,818 B2 | 4/2010 | Majumder |
| 7,716,225 B1 | 5/2010 | Dean et al. |
| 7,747,612 B2 | 6/2010 | Thun et al. |
| 7,756,887 B1 | 7/2010 | Haveliwala |
| 7,769,740 B2 | 8/2010 | Martinez et al. |
| 7,783,632 B2 | 8/2010 | Richardson et al. |
| 7,792,833 B2 | 9/2010 | Meyerzon |
| 7,801,885 B1 | 9/2010 | Verma |
| 7,809,716 B2 | 10/2010 | Wang et al. |
| 7,818,315 B2 | 10/2010 | Cucerzan et al. |
| 7,818,320 B2 | 10/2010 | Makeev |
| 7,836,058 B2 | 11/2010 | Chellapilla |
| 7,844,589 B2 | 11/2010 | Wang et al. |
| 7,849,089 B2 | 12/2010 | Zhang et al. |
| 7,853,557 B2 | 12/2010 | Schneider et al. |
| 7,856,446 B2 | 12/2010 | Brave et al. |
| 7,860,886 B2 | 12/2010 | Loftesness |
| 7,877,404 B2 | 1/2011 | Achan et al. |
| 7,895,177 B2 | 2/2011 | Wu |
| 7,925,498 B1 | 4/2011 | Baker et al. |
| 7,925,649 B2 | 4/2011 | Jeh et al. |
| 7,953,740 B1 | 5/2011 | Vadon et al. |
| 7,974,974 B2 | 7/2011 | Tankovich et al. |
| 7,987,185 B1 | 7/2011 | Mysen et al. |
| 8,001,136 B1 | 8/2011 | Papachristou et al. |
| 8,019,650 B2 | 9/2011 | Donsbach et al. |
| 8,024,326 B2 | 9/2011 | Tong et al. |
| 8,024,330 B1 | 9/2011 | Franco et al. |
| 8,027,439 B2 | 9/2011 | Zoldi et al. |
| 8,037,042 B2 | 10/2011 | Anderson et al. |
| 8,037,043 B2 | 10/2011 | Zoeter et al. |
| 8,037,086 B1 | 10/2011 | Upstill et al. |
| 8,051,061 B2 | 11/2011 | Niu et al. |
| 8,060,456 B2 | 11/2011 | Gao et al. |
| 8,060,497 B1 | 11/2011 | Zatsman et al. |
| 8,065,296 B1 | 11/2011 | Franz et al. |
| 8,069,182 B2 | 11/2011 | Pieper |
| 8,073,263 B2 | 12/2011 | Hull et al. |
| 8,073,772 B2 | 12/2011 | Bishop et al. |
| 8,073,867 B2 | 12/2011 | Chowdhury |
| 8,082,242 B1* | 12/2011 | Mysen et al. .................. 707/711 |
| 8,086,282 B2 | 12/2011 | Hellberg |
| 8,086,599 B1 | 12/2011 | Heymans |
| 8,090,717 B1 | 1/2012 | Bharat et al. |
| 8,126,839 B2 | 2/2012 | Chen et al. |
| 8,156,111 B2 | 4/2012 | Jones et al. |
| 8,171,041 B2 | 5/2012 | Bennett |
| 8,224,827 B2 | 7/2012 | Dean et al. |
| 8,239,370 B2 | 8/2012 | Wong et al. |
| 8,352,466 B2 | 1/2013 | Jones |
| 8,396,865 B1 | 3/2013 | Ie et al. |
| 8,412,699 B1 | 4/2013 | Mukherjee et al. |
| 8,447,760 B1 | 5/2013 | Tong et al. |
| 8,458,165 B2 | 6/2013 | Liao et al. |
| 8,498,974 B1 | 7/2013 | Kim et al. |
| 8,521,725 B1 | 8/2013 | Pearson et al. |
| 8,583,636 B1 | 11/2013 | Franz et al. |
| 8,738,596 B1 | 5/2014 | Kim et al. |
| 2001/0000356 A1 | 4/2001 | Woods |
| 2002/0034292 A1 | 3/2002 | Tuoriniemi et al. |
| 2002/0042791 A1 | 4/2002 | Smith et al. |
| 2002/0049752 A1 | 4/2002 | Bowman et al. |
| 2002/0103790 A1 | 8/2002 | Wang et al. |
| 2002/0123988 A1 | 9/2002 | Dean et al. |
| 2002/0133481 A1 | 9/2002 | Smith et al. |
| 2002/0165849 A1 | 11/2002 | Singh et al. |
| 2003/0009399 A1 | 1/2003 | Boerner |
| 2003/0018707 A1 | 1/2003 | Flocken |
| 2003/0028529 A1 | 2/2003 | Cheung et al. |
| 2003/0037074 A1 | 2/2003 | Dwork et al. |
| 2003/0078914 A1 | 4/2003 | Witbrock |
| 2003/0120654 A1 | 6/2003 | Edlund et al. |
| 2003/0135490 A1 | 7/2003 | Barrett et al. |

(56) References Cited

U.S. PATENT DOCUMENTS

| | | |
|---|---|---|
| 2003/0149704 A1 | 8/2003 | Yayoi et al. |
| 2003/0167252 A1 | 9/2003 | Odom et al. |
| 2003/0187837 A1* | 10/2003 | Culliss .......................... 707/3 |
| 2003/0195877 A1 | 10/2003 | Ford et al. |
| 2003/0204495 A1 | 10/2003 | Lehnert |
| 2003/0220913 A1 | 11/2003 | Doganata et al. |
| 2003/0229640 A1 | 12/2003 | Carlson et al. |
| 2004/0006456 A1 | 1/2004 | Loofbourrow |
| 2004/0006740 A1 | 1/2004 | Krohn et al. |
| 2004/0034632 A1 | 2/2004 | Carmel et al. |
| 2004/0049486 A1 | 3/2004 | Scanlon et al. |
| 2004/0059708 A1 | 3/2004 | Dean et al. |
| 2004/0083205 A1 | 4/2004 | Yeager |
| 2004/0093325 A1 | 5/2004 | Banerjee et al. |
| 2004/0119740 A1 | 6/2004 | Chang et al. |
| 2004/0122811 A1 | 6/2004 | Page |
| 2004/0153472 A1 | 8/2004 | Rieffanaugh, Jr. |
| 2004/0158560 A1 | 8/2004 | Wen et al. |
| 2004/0186828 A1 | 9/2004 | Yadav |
| 2004/0186996 A1 | 9/2004 | Gibbs et al. |
| 2004/0199419 A1 | 10/2004 | Kim et al. |
| 2004/0215607 A1 | 10/2004 | Travis, Jr. |
| 2005/0015366 A1 | 1/2005 | Carrasco et al. |
| 2005/0021397 A1 | 1/2005 | Cui et al. |
| 2005/0027691 A1 | 2/2005 | Brin et al. |
| 2005/0033803 A1 | 2/2005 | Vleet et al. |
| 2005/0050014 A1 | 3/2005 | Gosse et al. |
| 2005/0050027 A1* | 3/2005 | Yeh ..................... G06F 17/3087 |
| 2005/0055342 A1 | 3/2005 | Bharat et al. |
| 2005/0055345 A1 | 3/2005 | Ripley |
| 2005/0060290 A1 | 3/2005 | Herscovici et al. |
| 2005/0060310 A1 | 3/2005 | Tong et al. |
| 2005/0060311 A1 | 3/2005 | Tong et al. |
| 2005/0071741 A1 | 3/2005 | Acharya et al. |
| 2005/0102282 A1 | 5/2005 | Linden |
| 2005/0125376 A1 | 6/2005 | Curtis et al. |
| 2005/0160083 A1 | 7/2005 | Robinson |
| 2005/0192946 A1 | 9/2005 | Lu et al. |
| 2005/0198026 A1 | 9/2005 | Dehlinger et al. |
| 2005/0222987 A1 | 10/2005 | Vadon |
| 2005/0222998 A1 | 10/2005 | Driessen et al. |
| 2005/0240576 A1 | 10/2005 | Piscitello et al. |
| 2005/0240580 A1 | 10/2005 | Zamir et al. |
| 2005/0256848 A1 | 11/2005 | Alpert et al. |
| 2006/0036593 A1* | 2/2006 | Dean et al. .................. 707/4 |
| 2006/0047643 A1 | 3/2006 | Chaman |
| 2006/0069667 A1 | 3/2006 | Manasse et al. |
| 2006/0074903 A1 | 4/2006 | Meyerzon et al. |
| 2006/0089926 A1 | 4/2006 | Knepper et al. |
| 2006/0095421 A1 | 5/2006 | Nagai et al. |
| 2006/0106793 A1 | 5/2006 | Liang |
| 2006/0123014 A1 | 6/2006 | Ng |
| 2006/0173830 A1 | 8/2006 | Smyth et al. |
| 2006/0195443 A1 | 8/2006 | Franklin et al. |
| 2006/0200476 A1 | 9/2006 | Gottumukkala et al. |
| 2006/0200556 A1 | 9/2006 | Brave et al. |
| 2006/0227992 A1 | 10/2006 | Rathus et al. |
| 2006/0230040 A1 | 10/2006 | Curtis et al. |
| 2006/0259467 A1 | 11/2006 | Westphal |
| 2006/0259476 A1* | 11/2006 | Kadayam et al. ................ 707/3 |
| 2006/0293950 A1 | 12/2006 | Meek et al. |
| 2006/0294060 A1 | 12/2006 | Masuyama |
| 2007/0005575 A1 | 1/2007 | Dai et al. |
| 2007/0005588 A1 | 1/2007 | Zhang et al. |
| 2007/0016553 A1 | 1/2007 | Dumais |
| 2007/0038659 A1 | 2/2007 | Datar et al. |
| 2007/0050339 A1 | 3/2007 | Kasperski et al. |
| 2007/0061195 A1 | 3/2007 | Liu et al. |
| 2007/0061211 A1 | 3/2007 | Ramer et al. |
| 2007/0081197 A1 | 4/2007 | Omoigui |
| 2007/0106659 A1 | 5/2007 | Lu et al. |
| 2007/0112730 A1 | 5/2007 | Gulli et al. |
| 2007/0118533 A1 | 5/2007 | Ramer |
| 2007/0130370 A1 | 6/2007 | Akaezuwa |
| 2007/0156677 A1 | 7/2007 | Szabo |
| 2007/0172155 A1 | 7/2007 | Guckenberger |
| 2007/0180355 A1 | 8/2007 | McCall et al. |
| 2007/0192190 A1 | 8/2007 | Granville |
| 2007/0208730 A1 | 9/2007 | Agichtein et al. |
| 2007/0214044 A1 | 9/2007 | Lee |
| 2007/0214131 A1 | 9/2007 | Cucerzan et al. |
| 2007/0233653 A1 | 10/2007 | Biggs et al. |
| 2007/0233671 A1 | 10/2007 | Oztekin et al. |
| 2007/0255689 A1 | 11/2007 | Sun et al. |
| 2007/0260596 A1 | 11/2007 | Koran et al. |
| 2007/0260597 A1 | 11/2007 | Cramer et al. |
| 2007/0260624 A1 | 11/2007 | Chung |
| 2007/0266021 A1 | 11/2007 | Aravamudan et al. |
| 2007/0266439 A1 | 11/2007 | Kraft |
| 2007/0288450 A1 | 12/2007 | Datta et al. |
| 2008/0010143 A1 | 1/2008 | Kniaz et al. |
| 2008/0027913 A1 | 1/2008 | Chang et al. |
| 2008/0052219 A1 | 2/2008 | Sandholm et al. |
| 2008/0052273 A1 | 2/2008 | Pickens |
| 2008/0059453 A1 | 3/2008 | Laderman |
| 2008/0077570 A1 | 3/2008 | Tang et al. |
| 2008/0082518 A1 | 4/2008 | Loftesness |
| 2008/0091650 A1 | 4/2008 | Fontoura et al. |
| 2008/0104043 A1 | 5/2008 | Garg et al. |
| 2008/0114624 A1 | 5/2008 | Kitts |
| 2008/0114729 A1 | 5/2008 | Raman et al. |
| 2008/0114750 A1 | 5/2008 | Saxena et al. |
| 2008/0140699 A1 | 6/2008 | Jones et al. |
| 2008/0162475 A1 | 7/2008 | Meggs et al. |
| 2008/0183660 A1 | 7/2008 | Szulcewski |
| 2008/0189269 A1 | 8/2008 | Olsen |
| 2008/0208825 A1 | 8/2008 | Curtis et al. |
| 2008/0228442 A1 | 9/2008 | Lippincott et al. |
| 2008/0256050 A1 | 10/2008 | Zhang et al. |
| 2008/0313168 A1 | 12/2008 | Liu et al. |
| 2008/0313247 A1 | 12/2008 | Galvin |
| 2009/0006438 A1* | 1/2009 | Tunkelang et al. ............ 707/101 |
| 2009/0012969 A1 | 1/2009 | Rail et al. |
| 2009/0055392 A1* | 2/2009 | Gupta et al. ...................... 707/5 |
| 2009/0070194 A1 | 3/2009 | Song |
| 2009/0089657 A1 | 4/2009 | Davis et al. |
| 2009/0094073 A1 | 4/2009 | Cheung et al. |
| 2009/0157643 A1 | 6/2009 | Gollapudi et al. |
| 2009/0171943 A1 | 7/2009 | Majumder et al. |
| 2009/0182723 A1 | 7/2009 | Shnitko et al. |
| 2009/0187557 A1* | 7/2009 | Hansen et al. ..................... 707/5 |
| 2009/0228442 A1 | 9/2009 | Adams et al. |
| 2009/0287656 A1 | 11/2009 | Bennett |
| 2009/0313242 A1* | 12/2009 | Kodama ........................... 707/5 |
| 2010/0106706 A1 | 4/2010 | Rorex et al. |
| 2010/0131563 A1 | 5/2010 | Yin |
| 2010/0161591 A1 | 6/2010 | Jones et al. |
| 2010/0205541 A1 | 8/2010 | Rapaport et al. |
| 2010/0228738 A1 | 9/2010 | Mehta et al. |
| 2010/0241472 A1 | 9/2010 | Hernandez |
| 2010/0299317 A1* | 11/2010 | Uy ................. 707/706 |
| 2010/0325131 A1 | 12/2010 | Dumais et al. |
| 2011/0029517 A1 | 2/2011 | Ji et al. |
| 2011/0087656 A1* | 4/2011 | Oh et al. ....................... 707/727 |
| 2011/0087966 A1 | 4/2011 | Leviathan et al. |
| 2011/0179093 A1 | 7/2011 | Pike et al. |
| 2011/0219025 A1 | 9/2011 | Lipson et al. |
| 2011/0264670 A1* | 10/2011 | Banerjee et al. ............. 707/749 |
| 2011/0282906 A1 | 11/2011 | Wong |
| 2011/0295844 A1 | 12/2011 | Sun et al. |
| 2011/0295879 A1 | 12/2011 | Logis et al. |
| 2012/0011148 A1 | 1/2012 | Rathus et al. |
| 2012/0191705 A1 | 7/2012 | Tong et al. |

FOREIGN PATENT DOCUMENTS

| | | |
|---|---|---|
| WO | WO 01/67297 | 9/2001 |
| WO | WO 2004/059514 | 7/2004 |

OTHER PUBLICATIONS

Agichtein, et al; *Learning User Interaction Models for Predicting Web Search Result Performances*; Aug. 2006; Proceedings of the

(56) References Cited

OTHER PUBLICATIONS

Twenty-Ninth Annual International ACM SIGIR Conference on Research and Development in Information Retrieval, p. 3-10.
Boyan et al.; *A Machine Learning Architecture for Optimizing Web Search Engines*; Aug. 1996; Internet-based information systems—Workshop Technical Report—American Association for Artificial Intelligence, p. 1-8.
Burke, Robin, Integrating Knowledge'based and Collaborative-filtering Recommender Systems, AAAI Technical Report WS-99-01. Compilation copyright © 1999, AAAI (www.aaai.org), pp. 69-72.
Cutrell, et al.; *Eye tracking in MSN Search: Investigating snippet length, target position and task types*; 2007; Conference on Human Factors in Computing Systems—Proceedings of the SIGCHI Conference on Human Factors in Computing Systems.
Diligenti, et al., *Users, Queries and Documents: A Unified Representation for Web Mining*, wi-iat, vol. 1, 2009 IEEE/WIC/ACM International Joint Conference on Web Intelligence and Intelligent Agent Technology, 2009, pp. 238-244.
Hofmann, Thomas, *Latent Semantic Models for Collaborative Filtering*, ACM Transactions on Information Systems, vol. 22, No. 1, Jan. 2004, pp. 89-115.
Grčar, Miha, *User Profiling: Collaborative Filtering*, SIKDD 2004, Oct. 12-15, 2004, Ljubljana, Slovenia, 4 pages.
Kelly, et al.; *Implicit Feedback for Inferring User Preference: A Bibliography*; SIGIR Forum, vol. 37, No. 2 (2003), pp. 18-28.
Linden, Greg et al., *Amazon.com Recommendations: Item-to-Item Collaborative Filtering*, [online], http://computer.org/internet/, IEEE Internet Computing, Jan.-Feb. 2003, IEEE Computer Society, pp. 76-80.
Nicole, Kristen, *Heeii is StumbleUpon Plus Google Suggestions*, [online], Retrieved from the Internet http://mashable.com/2007/05/15/heeii/, 11 pages.
Lemire, Daniel, *Scale and Translation Invariant Collaborative Filtering Systems*, Published in Information Retrieval, 8(1), pp. 129-150, 2005.
Radlinski, et al., *Query Chains: Learning to Rank from Implicit Feedback*, KDD '05, Aug. 21-24, 2005, Chicago, Illinois, USA, 10 pages.
Schwab, et al., *Adaptivity through Unobstrusive Learning*, 2002, 16(3), pp. 5-9.
Stoilova, Lubomira et al., *GiveALink: Mining a Semantic Network of Bookmarks for Web Search and Recommendation*, LinkKDD '05, Aug. 21, 2005, Chicago, IL, USA, 8 pages.
Xiao, et al., *Measuring Similarity of Interests for Clustering Web-Users*, ADC, 2001, p. 107-114.
Xie et al., *Web User Clustering from Access Log Using Belief Function*, K-CAP '01, Oct. 22-23, 2001, Victoria, British Columbia, Canada, pp. 202-208.
Yu et al., *Selecting Relevant Instances for Efficient and Accurate Collaborative Filtering*, CIKM '01, Nov. 5-10, 2001, Atlanta, Georgia, pp. 239-246.
Zeng et al., *Similarity Measure and Instance Selection for Collaborative Filtering*, WWW '03, May 20-24, 2003, Budapest, Hungary, pp. 652-658.
Joachims, "Evaluating Search Engines Using Clickthrough Data", Cornell University, Department of Computer Science, Draft, Feb. 19, 2002, 13 pages.
Joachims; Optimizing search engines using clickthrough data; 2002; Proceedings of the ACM SIGKDD International Conference on Knowledge Discovery and Data Mining, p. 133-142, 10 pages.
Jansen et al., "An Analysis of Web Documents Retrieved and Viewed", School of Information Sciences and Technology, The Pennsylvania State University, the 4th International Conference on Internet Computing, Las Vegas, Nevada, pp. 65-69, Jun. 23-26, 2003, 5 pages.
U.S. Appl. No. 14/143,622, filed Dec. 30, 2013, Kim et al.
U.S. Appl. No. 11/870,893, filed Oct. 11, 2007, McDonnell.
U.S. Appl. No. 13/620,528, filed Sep. 14, 2012, Kim et al.
U.S. Appl. No. 13/953,162, filed Jul. 29, 2013, Kim et al.
U.S. Appl. No. 12/572,739, filed Oct. 2, 2013, McDonnell et al.
U.S. Appl. No. 12/632,279, filed Dec. 7, 2009, Serboncini et al.
U.S. Appl. No. 13/476,875, filed May 21, 2012, Lopatenko et al.
U.S. Appl. No. 12/723,973, filed Mar. 15, 2010, Nerurkar.
U.S. Appl. No. 12/623,276, filed Nov. 20, 2009, Kim et al.
U.S. Appl. No. 13/618,111, filed Sep. 14, 2012, Kim et al.
U.S. Appl. No. 12/718,634, filed Mar. 5, 2010, Kim et al.
U.S. Appl. No. 12/842,345, filed Jul. 23, 2010, Chen et al.
U.S. Appl. No. 12/982,633, filed Dec. 30, 2010, Adams et al.
U.S. Appl. No. 13/608,278, filed Sep. 10, 2012, Kuramochi et al.
Soumen Chakrabarti, et al. "Enhanced Topic Distillation using Text, Markup tags, and Hyperlinks". ACM, Sep. 9-12, 2001, pp. 208-216.
Gabriel Somlo et al., "Using Web Hepler Agent Profiles in Query Generation", ACM, Jul. 2003, pp. 812-818.
Bar-Llan et al., "Presentation Bias is Significant in Determining User Preference for Search Results—A User Study"; Journal of the American Society for Information Science and Technology, vol. 60, Issue 1 (p. 135-149), Sep. 2008, 15 pages.
Bar-Llan et al.; ""Methods for comparing rankings of search engine results""; Computer Networks: The International Journal of Computer and Telecommunications Networking, Jul. 2006, vol. 50, Issue 10, 19 pages.
Boldi, et al.; The Query-flow Graph: Model and Applications; CKIM '08, Oct. 26-30, Napa Valley, California, USA, pp. 609-617.
Burke, Robin, Integrating Knowledge-based and Collaborative-filtering Recommender Systems, AAAI Technical Report WS-99-01. Compilation copyright © 1999, AAAI (www.aaai.org), pp. 69-72.
Craswell, et al.; Random Walks on the Click Graph; Jul. 2007; SIGIR '07, Amsterdam, the Netherlands, 8 pages.
Google News archive, Jul. 8, 2003, Webmasterworld.com, [online] Retrieved from the Internet http://www.webmasterwolrd.com/forum3/15085.htm [retrieved on Nov. 20, 2009] 3 pages.
Joachims et al., "Search Engines that Learn from Implicit Feedback"; Aug. 2007, IEEE Computer Society.
Joachims, T., Evaluating retrieval performance using clickthrough data. Proceedings of the SIGIR Workshop on Mathematical/Formal Methods in Information Retrieval; 2002, Aug. 12-15; Tampere, Finland, 18 pages.
Joachims; Optimizing search engines using clickthrough data; 2002; Proceedings of the ACM SIGKDD International Conference on Knowledge Discovery and Data Mining, p. 133-142.
U.S. Appl. No. 11/556,143, filed Nov. 2, 2006, in Office Action mailed Apr. 20, 2011, 18 pages.
U.S. Appl. No. 11/556,143, filed Nov. 2, 2006, in Office Action mailed Jan. 25, 2010, 14 pages.
U.S. Appl. No. 11/556,143, filed Nov. 2, 2006, in Office Action mailed Jul. 6, 2010, 20 pages.
U.S. Appl. No. 11/685,095, filed Mar. 12, 2007, in Office Action mailed Apr. 13, 2011, 31 pages.
U.S. Appl. No. 11/685,095, filed Mar. 12, 2007, in Office Action mailed Feb. 25, 2009, 21 pages.
U.S. Appl. No. 11/685,095, filed Mar. 12, 2007, in Office Action mailed Feb. 8, 2010, 31 pages.
U.S. Appl. No. 11/685,095, filed Mar. 12, 2007, in Office Action mailed Sep. 10, 2009, 23 pages.
U.S. Appl. No. 11/556,086 filed Nov. 2, 2006, in Office Action mailed Jun. 23, 2010, 21 pages.
W3C, URIs, URLs and URNs: Classification and Recommendations 1.0, Report from the joint W3C/IETF URI Planning Interest Group, Sep. 21, 2001, 8 pages.
Xiao, et al., Measuring Similarity of Interests for Clustering Web-Users, ADC, 2001, pp. 107-114.
Zeng, et al., "Learning to Cluster Web Search Results", SIGIR '04, Proceedings of the 27th Annual International ACM SIGIR conference on research and development in information retrieval, 2004.
Australian Patent Office Non-Final Office Action in AU App. Ser. No. 2004275274, mailed Feb. 3, 2010, 2 pages.
Dan Olsen et al., "Query-by-critique: Spoken Language Access to Large Lists", ACM, Oct. 2002, pp. 131-140.

(56) References Cited

OTHER PUBLICATIONS

Susan Gauch et al., "A Corpus Analysis Approach for Automatic Query Expansion and its Extension to Multiple Databases", ACM, Jul. 1999, pp. 250-269.
Nicolas Bruno et al., "Top-K Selection Queries over Relational Databases: Mapping Strategies and Performance Evaluation", ACM, Jun. 2002, pp. 153-187.
Ji-Rong Wen et al., "Query Clustering using User Logs", ACM, Jan. 2002, pp. 59-81.
Brin, S. and L. Page, The Anatomy of a Large-Scale Hypertextual Web Search Engine, Computer Science Department, Apr. 1998.
International Search Report and Written Opinion for Application No. PCT/US2004/029615, dated Jan. 19, 2005, 8 pages.
Hungarian Patent Office, International Search Report and Written Opinion for Application No. 200806756-3, dated Nov. 19, 2010 12 pages.
Authorized Officer Athina Nickitas-Etienne, International Preliminary Report and Written Opinion for Application No. PCT/US2004/029615, mailed Mar. 23, 2006.
Indian Office Action in Indian Application No. 686/KOLNP/2006, mailed Jun. 3, 2008, 2 pages
Danish Examiner Henrik Ebbesen Jensen, Danish Search Report and Written Opinion for Application No. 200601630-7, dated Jun. 21, 2007, 15 pages.
Jones et al., "Pictures of Relevance: A Geometric Analysis of Similarity Measures", Journal of the American Society for Information Science, Nov. 1987, 23 pages.
Kaplan et al., "Adaptive Hypertext Navigation Based on User Goals and Context", User Modeling and User-Adapted Interaction 2, Sep. 1, 1993; pp. 193-220, 28 pages.
Liddy et al., "A Natural Language Text Retrieval System With Relevance Feedback", 16th National Online, May 2-6, 1995, 3 pages.
"Personalizing Search via Automated Analysis of Interests and Activities," by Teevan et al. IN: SIGIR'05 (2005). Available at: ACM.
Baeza-Yates, Ricardo, Carlos Hurtado, and Marcelo Mendoza. "Query recommendation using query logs in search engines." Current Trends in Database Technology—EDBT 2004 Workshops. Springer Berlin Heidelberg, 2005.
Velez, Bienvenido, et al. "Fast and effective query refinement." ACM SIGIR Forum. vol. 31. No. SI. ACM, 1997.
Mandala, Rila, Takenobu Tokunaga, and Hozumi Tanaka. "Combining multiple evidence from different types of thesaurus for query expansion." Proceedings of the 22nd annual international ACM SIGIR conference on Research and development in information retrieval. ACM, 1999.
"Dynamic Adaptation Strategies for Long-Term and Short-Term User Profile," by Li et al. IN: LNCS 4505 pp. 228-240 (2007). Available at: Springer.
3. "An Adaptive Algorithm for Learning Changes in User Interests," by Widyantoro et al. IN: CIKM'99 (1999). Available at: ACM.

\* cited by examiner

ACCENTUATING SEARCH RESULTS

BACKGROUND

The present disclosure relates to digital data processing and, in particular, to using data that represents previously submitted user queries to accentuate search results.

Internet search engines aim to identify documents or other items that are relevant to a user's needs and to present the documents or items in a manner that is most useful to the user. Such activity often involves a fair amount of mind-reading inferring from various clues what the user wants. Certain clues may be user specific. For example, knowledge that a user is making a request from a mobile device, and knowledge of the location of the device, can result in much better search results for such a user.

Clues about a user's needs may also be more general. For example, search results can have an elevated importance, or inferred relevance, if a number of other search results link to them. If the linking results are themselves highly relevant, then the linked-to results may have a particularly high relevance. Such an approach to determining relevance may be premised on the assumption that if authors of web pages felt that another web site was relevant enough to be linked to then web searchers would also find the site to be particularly relevant. In short, the web authors "vote up" the relevance of the sites.

Other various inputs may be used instead of, or in addition to, such techniques for determining and ranking search results. For example, user reactions to particular search results or search result lists may be gauged, so that results on which users often click will receive a higher ranking. The general assumption under such an approach is that searching users are often the best judges of relevance, so that if they select a particular search result, it is likely to be relevant, or at least more relevant than the presented alternatives.

SUMMARY

This specification describes technologies relating to ranking search results.

In general, one or more aspects of the subject matter described in this specification can be embodied in one or more methods for processing query information. The methods include receiving documents responsive to a query, each document having an associated score indicative of the document's relevance to the query. The methods include determining, for a plurality of the associated scores, a distribution of the scores along a dimension that measures trustworthiness of the scores. The methods include reducing each of one or more of the plurality of associated scores by an amount determined based on the score's respective trustworthiness among an arrangement of scores in the distribution. The methods also include ranking the documents to account for the reduced scores. Other implementations of this aspect include corresponding systems, apparatus, and computer program products.

These and other embodiments can optionally include one or more of the following features. The distribution may be a frequency distribution and the amount may be determined based on a distance between a lowest and a highest score in the distribution. The amount may be determined based on a number of intervals in the distribution and the score's trustworthiness. The amount may be determined based on a shape of the distribution and the score's trustworthiness. Each of the associated scores may include one or more score components. Reducing each of one or more of the plurality of associated scores by the amount may include reducing a first score component for each score. The first score component may represents an amount added to an information retrieval score for an associated document.

The methods may also include providing the ranked documents to a client. The score's respective trustworthiness may be determined by a metric that calculates a degree of trustworthiness for the score. Trustworthiness of a score may be based on a language of the score's associated document. Trustworthiness of a score may be based on the similarity between the query and a previous query. Trustworthiness of a score may based on a country from which the query was submitted and the country in which the documents were created.

Particular embodiments of the described subject matter can be implemented to realize one or more of the following advantages. Search result quality can be improved. Search result scores can be modified based on differences in the reliability of the source of the scores.

The details of one or more implementations are set forth in the accompanying drawings and the description below. Other features, aspects, and advantages will become apparent from the description, the drawings, and the claims.

DESCRIPTION OF THE DRAWINGS

Like reference numbers and designations in the various drawings indicate like elements.

DETAILED DESCRIPTION

Figure 1:
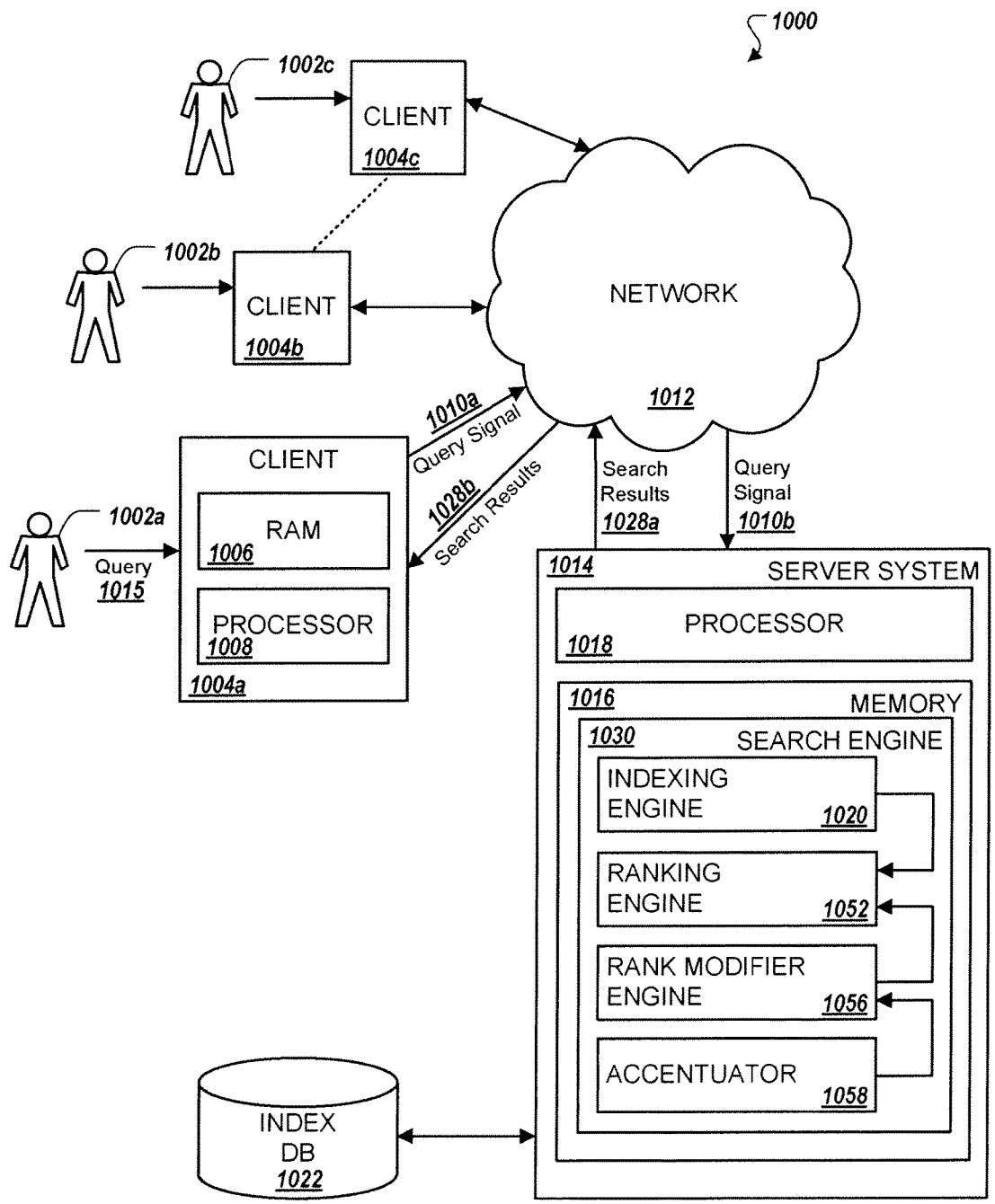
FIG. 1 shows an example information retrieval system.

FIG. 1 shows an example system 1000 for improving the relevance of results obtained from submitting search queries as can be implemented in an internet, intranet, or other client/server environment. The system 1000 is an example of an information retrieval system in which the systems, components and techniques described below can be implemented. Although several components are illustrated, there may be fewer or more components in the system 1000. Moreover, the components can be distributed on one or more computing devices connected by one or more networks or other suitable communication mediums.

A user 1002 (1002a, 1002b, 1002c) can interact with the system 1000 through a client device 1004 (1004a, 1004b, 1004c) or other device. For example, the client device 1004 can be a computer terminal within a local area network (LAN) or wide area network (WAN). The client device 1004 can include a random access memory (RAM) 1006 (or other memory and/or a storage device) and a processor 1008. The processor 1008 is structured to process instructions within the system 1000. In some implementations, the processor 1008 is a single-threaded processor. In other implementations, the processor 1008 is a multi-threaded processor. The processor 1008 can include multiple processing cores and is structured to process instructions stored in the RAM 1006 (or other memory and/or a storage device included with the client device 1004) to display graphical information for a user interface.

A user 1002*a* can connect to a search engine 1030 within a server system 1014 to submit a query 1015. When the user 1002*a* submits the query 1015 through an input device attached to a client device 1004*a*, a client-side query signal 1010*a* is sent into a network 1012 and is forwarded to the server system 1014 as a server-side query signal 1010*b*. Server system 1014 can be one or more server devices in one or more locations. The server system 1014 includes a memory device 1016, which can include the search engine 1030 loaded therein. A processor 1018 is structured to process instructions within the server system 1014. These instructions can implement one or more components of the search engine 1030. The processor 1018 can be a single-threaded processor or a multi-threaded processor, and can include multiple processing cores. The processor 1018 can process instructions stored in the memory 1016 related to the search engine 1030 and can send information to the client device 1004*a*, through the network 1012, to create a graphical presentation in a user interface of the client device 1004*a* (e.g., a search results web page displayed in a web browser).

The server-side query signal 1010*b* is received by the search engine 1030. The search engine 1030 uses the information within the user query 1015 (e.g. query terms) to find relevant documents. The search engine 1030 can include an indexing engine 1020 that actively searches a corpus (e.g., web pages on the Internet) to index the documents found in that corpus, and the index information for the documents in the corpus can be stored in an index database 1022. This index database 1022 can be accessed to identify documents related to the user query 1015. Note that, an electronic document (which for brevity will simply be referred to as a document) does not necessarily correspond to a file. A document can be stored in a portion of a file that holds other documents, in a single file dedicated to the document in question, or in multiple coordinated files.

The search engine 1030 can include a ranking engine 1052 to rank the documents related to the user query 1015. The ranking of the documents can be performed using traditional techniques for determining an information retrieval (IR) score for indexed documents in view of a given query. The relevance of a particular document with respect to a particular search term or to other provided information may be determined by any appropriate technique. For example, the general level of back-links to a document that contains matches for a search term may be used to infer a document's relevance. In particular, if a document is linked to (e.g., is the target of a hyperlink) by many other relevant documents (e.g., documents that also contain matches for the search terms), it can be inferred that the target document is particularly relevant. This inference can be made because the authors of the pointing documents presumably point, for the most part, to other documents that are relevant to their audience.

If the pointing documents are in turn the targets of links from other relevant documents, they can be considered more relevant, and the first document can be considered particularly relevant because it is the target of relevant (or even highly relevant) documents. Such a technique may be the determinant of a document's relevance or one of multiple determinants. The technique is exemplified in some systems that treat a link from one web page to another as an indication of quality for the latter page, so that the page with the most such quality indicators is rated higher than others. Appropriate techniques can also be used to identify and eliminate attempts to cast false votes so as to artificially drive up the relevance of a page.

To further improve such traditional document ranking techniques, the ranking engine 1052 can receive an additional signal from a rank modifier engine 1056 to assist in determining an appropriate ranking for the documents. The rank modifier engine 1056 provides one or more prior models, or one or more measures of relevance for the documents based on one or more prior models, which can be used by the ranking engine 1052 to improve the search results' ranking provided to the user 1002. In general, a prior model represents a background probability of document result selection given the values of multiple selected features, as described further below. The rank modifier engine 1056 can perform one or more of the operations described below to generate the one or more prior models, or the one or more measures of relevance based on one or more prior models.

Various types of information may be provided to the rank modifier engine 1056 for improving the ranking of documents. For example, one or more dimensions associated with a search requestor may be identified and used to adjust rankings of search results. To determine such dimensions of a search requestor, and to adjust rankings based on the dimensions, the search engine 1030 can include an accentuator 1058 that may implement one or more identification and adjustment techniques. For example, the dimensions may be representative of characteristics associated with the search requestor. Such characteristics can include location of the requestor (e.g., country, region, state, city, etc.), language (e.g., English, Spanish, etc.), demographics (e.g., gender, age, etc.), areas of interest (e.g., sports, movies, etc.), and personal traits (e.g., profession, level of education, etc.), to name a few examples. Characteristics may be provided by the search requestor, or may be inferred by analyzing data related to the search request or a series of search requests, or determined in some other manner. Additionally, information related to interactions between the search requestor and search results (e.g., click data, query refinement, etc.) may be used to adjust the dimensions and to adjust search result rankings. Once identified, data representing the identified dimensions may be cataloged in a database (e.g., the index db 1022). Further, the identified user dimensions may be used for various applications such as providing assistance during future search sessions performed by the user 1002*a* or other users. Search result scoring and ranking (e.g., as performed by the ranking engine 1020 or the rank modifier engine 1056) can be adjusted to account for dimensions related to the user 1002*a* or similar users.

In some arrangements, the dimensions of a user may be ordered based on which dimensions are most likely to produce good search results. For example, some dimensions may be considered inherently more accurate (e.g. profession may be considered a better indicator than level of education). In other scenarios, one dimension may be determined to have a stronger influence on a particular query (e.g. gender may have a strong influence on the query "village"). In some arrangements, dimensions may be ranked based on the amount of information there is supporting the dimension. For example, dimensions which influence a broad range of queries may be considered superior to dimensions which influence fewer queries. In other arrangements, all dimensions may be used to influence search results.

In some arrangements, a number of top dimensions may be applied to the query in order to provide diversity in the search results. For example, if a search requester searches for "fox", one dimension indicates that the search requester is looking for the animal fox, another dimension indicates that the search requester is looking for Megan Fox, and yet another dimension indicates that the search requester is looking for the clothing company (by the same name). The rank modifier engine may adjust the ranking of the results such that the best result from each of these dimensions shows up as the top results thereby providing a range of result options.

The search engine 1030 can forward the final, ranked result list within a server-side search results signal 1028a through the network 1012. Exiting the network 1012, a client-side search results signal 1028b can be received by the client device 1004a where the results can be stored within the RAM 1006 and/or used by the processor 1008 to display the results on an output device for the user 1002a.

Figure 2:
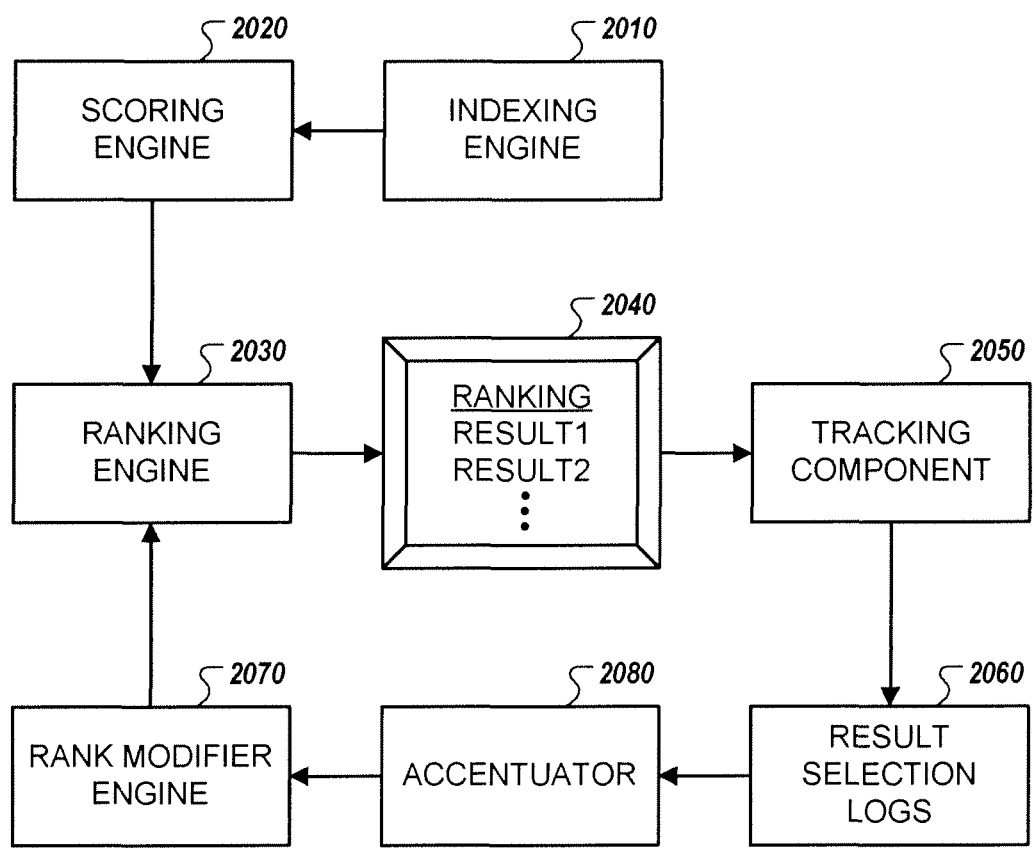
FIG. 2 shows example components of an information retrieval system.

FIG. 2 shows example components of an information retrieval system. These components can include an indexing engine 2010, a scoring engine 2020, a ranking engine 2030, a rank modifier engine 2070, and an accentuator 2080. The indexing engine 2010 can function as described above for the indexing engine 1020. In addition, the scoring engine 2020 can generate scores for document results based on many different features, including content-based features that link a query to document results, and query-independent features that generally indicate the quality of document results. The content-based features can include aspects of document format, such as query matches to title or anchor text in an HTML (Hyper Text Markup Language) page. The query-independent features can include aspects of document cross-referencing, such as a rank of the document or the domain. Moreover, the particular functions used by the scoring engine 2020 can be tuned, to adjust the various feature contributions to the final IR score, using automatic or semi-automatic processes.

The ranking engine 2030 can produce a ranking of document results 2040 for display to a user based on IR scores received from the scoring engine 2020 and one or more signals from the rank modifier engine 2070. The rank modifier engine 2070 can adjust rankings at least in part based on data received from the accentuator 2080. Along with being provided data from the result selection logs 2060, other sources may provide information to the accentuator 2080. For example, queries entered into a user interface may be provided to the accentuator 2080. In this particular example, the accentuator 2080 provides information to the rank modifier engine 2070 for ranking adjustments, however other architectures may be implemented. For example, dimensional information may be provided by the accentuator 2080 to the indexing engine 2010 or one or more other components of the information retrieval system. A tracking component 2050 can be used to record information regarding individual user selections of the results presented in the ranking 2040. For example, the tracking component 2050 can be embedded JavaScript code included in a web page ranking 2040 that identifies user selections (clicks) of individual document results and also identifies when the user returns to the results page, thus indicating the amount of time the user spent viewing the selected document result. In other implementations, the tracking component 2050 can be a proxy system through which user selections of the document results are routed, or the tracking component can include pre-installed software at the client (e.g., a toolbar plug-in to the client's operating system). Other implementations are also possible, such as by using a feature of a web browser that allows a tag/directive to be included in a page, which requests the browser to connect back to the server with message(s) regarding link(s) clicked by the user.

The recorded information can be stored in the result selection log(s) 2060. The recorded information can include log entries that indicate, for each user selection, the query (Q), the document (D), the time (T) on the document, the language (L) employed by the user, and the country (C) where the user is likely located (e.g., based on the server used to access the IR system). Other information can also be recorded regarding user interactions with a presented ranking, including negative information, such as the fact that a document result was presented to a user, but was not clicked, position(s) of click(s) in the user interface, IR scores of clicked results, IR scores of all results shown before the clicked result, the titles and snippets shown to the user before the clicked result, the user's cookie, cookie age, IP (Internet Protocol) address, user agent of the browser, etc. Still further information can be recorded, such as described below during discussion of the various features that can be used to build a prior model. Moreover, similar information (e.g., IR scores, position, etc.) can be recorded for an entire session, or multiple sessions of a user, including potentially recording such information for every click that occurs both before and after a current click.

The information stored in the result selection log(s) 2060 can be used by one or more components of the information retrieval system. For example, information could be provided to the accentuator 2080 and the rank modifier engine 2070 in generating the one or more signals to the ranking engine 2030. In general, a wide range of information can be collected and used to modify or tune the click signal from the user to make the signal, and the future search results provided, a better fit for the user's needs. Thus, user interactions with the rankings presented to the users of the information retrieval system can be used to improve future rankings. Additionally, one or more dimensions representative of user characteristics can be used to modify rankings. In some arrangements, the user interaction and the dimension data may be provided to one or more server systems (e.g., server system 1014) for use and storage (e.g., database 1022) for later retrieval.

The components shown in FIG. 2 can be combined in various manners and implemented in various system configurations. For example, the scoring engine 2020 and the ranking engine 2030 can be merged into a single ranking engine, such as the ranking engine 1052 of FIG. 1. The accentuator 2080, the rank modifier engine 2070 and the ranking engine 2030 can also be merged, and in general, a ranking engine includes any software component that generates a ranking of document results after a query. Moreover, a ranking engine can be included in a client system in addition to (or rather than) in a server system.

Figure 3:
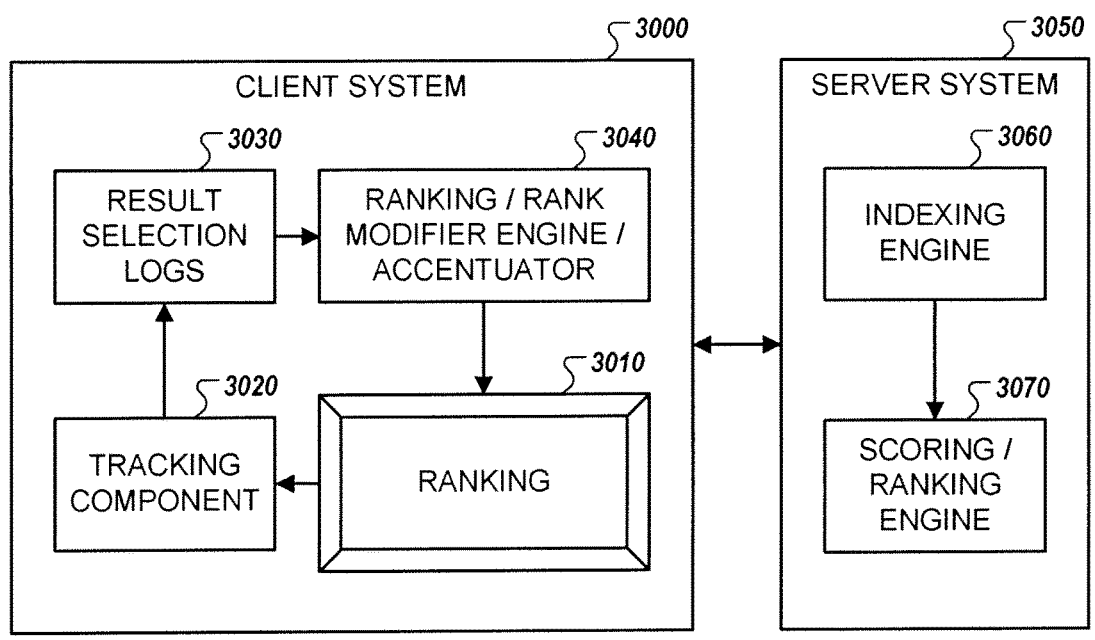
FIG. 3 shows another example information retrieval system and components.

FIG. 3 shows another example information retrieval system. In this system, a server system 3050 includes an indexing engine 3060 and a scoring/ranking engine 3070. A client system 3000 includes a user interface for presenting a ranking 3010, a tracking component 3020, result selection log(s) 3030 and a ranking/rank modifier engine/accentuator 3040. For example, the client system 3000 can include a company's enterprise network and personal computers, in which a browser plug-in incorporates the ranking/rank modifier engine/accentuator 3040. When an employee in the company initiates a search on the server system 3050, the scoring/ranking engine 3070 can return the search results along with either an initial ranking or the actual IR scores for the results. The browser plug-in can then re-rank the results locally based on tracked page selections for the company-specific user base.

Figure 4:
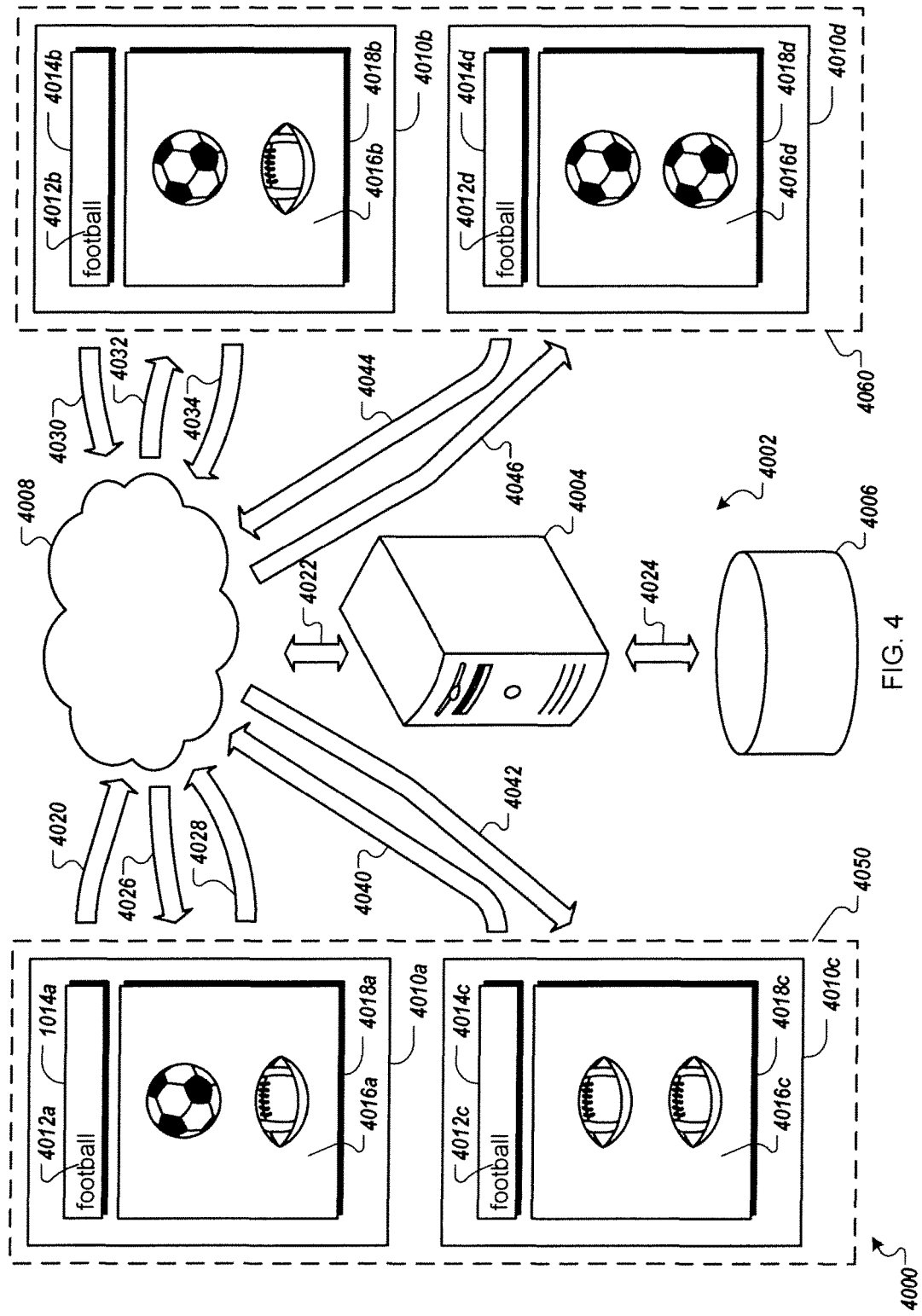
FIG. 4 illustrates a set of information retrieval search sessions.

Referring to FIG. 4, operations of an exemplary set of search sessions of an exemplary information retrieval system 4000 are illustrated. Similar to the systems shown in FIGS. 1, 2 and 3, the information retrieval system 4000 shown in FIG. 4 can provide relevant results for search queries. For example, similar to client device 1004 (shown in FIG. 1), client side systems 4010a, 4010b, 4010c and 4010d can enable users to enter search queries and interact with search results. Also, similar to server system 1014 (also shown in FIG. 1), a server side system 4002 can process search queries and generate search results that are correspondingly provided to any of the client side systems 4010a-d. Being scalable, more or fewer client side systems and server side systems may be included in the information retrieval system 4000.

The client side systems 4010a-d may each include a query interface 4014a-d (e.g., text entry control, type-ahead search control, selectable list, etc.) enabling a user to provide search queries. The client side systems 4010a-d may also each include a results interface 4018a-d that enables a user to view and interact with query results. Query result content may be provided in various types of representations; for example, such content may be provided in links (e.g., uniform resource locators (URLs)), text (e.g., relevant content portions, summaries, etc.), media (e.g., graphics, video, audio, etc.), individually or in combination. Any of the results interfaces 4018a-d may be provided by one or more output devices (e.g., video display, audio playback system, etc.). Various types of equipment may be included in the server side system 4002 to access, process, and store content. For example, one or more servers (represented by a server 4004) and one or more data stores (represented by a data store 4006) may be incorporated into the server side system 4002. One or more communication techniques may be implemented for exchanging data among the client side systems 4010a-d, the server side system 4002, and other data sources (not shown). For example, one or more networking techniques may be used to provide communication through a network 4008 (e.g., the Internet) such as wired or wireless (or a combination of wired and wireless) connections.

To search for desired content (e.g., documents, video, audio, etc.) a user typically provides information representative of a query to any of the client side systems 4010a-d. For example, a search session can be established in which multiple user queries are entered over a period of time (e.g., ten seconds, a minute, ten minutes, thirty minutes, an hour, two hours, etc.). Additionally, a query session may also include user interactions (e.g., clicking, scrolling, viewing, etc.) with search results based on the entered query. Upon entering a query and receiving a set of query results (e.g., links), the user may interact with the results by clicking one or more links, for example, based on associated information (e.g., text descriptions, media, etc.). Click data, which may be represented by selecting a link, visiting a resource (e.g., a web page) associated with a selected link for an amount of time (e.g., five seconds, one minute, five minutes, etc.), or other type of user interaction may be collected during a search session. Lack of user interactions, for example, proceeding to another set of search results without selecting a link, may be collected and stored. To store the collected information one or more techniques may be implemented, for example, a web browser cookie may be maintained by any of the client systems 4010a-d that represents the collected information or a portion of the information.

Along with collecting user interactions (or lack of interactions) detected during a search session, other information may be collected. For example, collected information may represent one or more dimensions representative of characteristics associated with a user of any of the client side systems 4010a-d. By identifying the particular user dimensions or dimensions commonly shared among multiple users, this information could be used to assist subsequent searches during the same search session or during future search sessions. If a group of users commonly sharing a particular dimension are found to generally prefer a particular query result (e.g., based on click data, interactions with results, etc.), for example, the information retrieval system may associate the result preferences with the dimension. For example, statistics (e.g., counts, averages, time-related data, etc.) related to query result preferences may be gathered and stored (e.g., in the data store 4006) in association with one or more identified dimensions. The statistics may be used to modify search result rankings for users associated with the dimensions, for example.

One or more techniques and methodologies may be implemented, alone or in combination, to identify user dimensions. For example, a user locality may be determined from a domain specified by a user. If a user specifies a search domain such as "google.co.uk", for example, an inference may be made that the user is from the United Kingdom. As another example, a user locality may be determined by identifying information (e.g., an IP address) associated with a user device. A user language may be determined by cross-referencing provided search query terms with various language dictionaries, for example. In another example, a user language may be determined by referencing a browser's language setting. Dimensions such as demographics (e.g., gender, age, etc.) and other traits (e.g., profession, level of education, etc.), for example, may be inferred by examining search queries and interactions from a search session. For example, it may be surmised that a user providing search queries including medical terminology (as opposed to common terminology) and interacting with search results of a technical nature (e.g., medical journal articles, etc.) may be a member of the medical profession. Additionally, particular words and spelling patterns may be detected for identifying user dimensions. For example, such words and spelling patterns may be indicative of a particular nationality (e.g., using the spelling "color" vs. "colour" may indicate an American nationality). As another example, frequent correct or incorrect spelling may be indicative of a high or low level of education. Such inferences may be used to identify one or more dimensions associated with the user and the identified dimensions may be used to provide more relevant search results to the user, for example.

As shown in FIG. 4, a search session may be initiated by a query being provided by a user. In this example, a search session is initiated by a search query 4012a (e.g., "football") being entered via the query interface 4014a of the client side system 4010a. As shown by process arrows 4020 and 4022, the search query 4012a and dimensional information associated with a user (e.g., location, language, etc.) may be sent to the server side system 4002 via the network 4008. The server side system 4002 can process the search query 4012a and related information, for example by using one or more software modules (e.g., a search engine) executed by the server 4004. As shown by process arrow 4024, data (e.g., index information, dimensional information, search session statistics, etc.) may be retrieved from or stored in the data store 4006 and can be used by the server 4004 for providing a set of query results. Data store 4006 is representative of various types of information sources that may be in communication with the server 4004. For example, one or more storage devices (e.g., hard drives, etc.), servers, and computing device equipment may be directly or indirectly (e.g., via one or more networks) in communication with the server 4004. As shown by process arrows 4022 and 4026, search results may be sent to the client side system 4010a via the network 4008. Upon receipt, a set of search results 4016a may be presented to the user via the results interface 4018a. For illustrative purposes, the search results 4016a (and search results 4016b-d) are shown as graphical representations, however, other representations (e.g., text, links, etc) may be shown individually or in combination with the graphics.

Multiple client devices may conduct concurrent search sessions in the informational retrieval system 4000. In this example, a user of the client side system 4010b may initiate a search session by entering a search query 4012b (e.g., "football") via the query interface 4014b. As shown by process arrows 4030 and 4022, the search query 4012b and dimensional informational associated with the user may be sent to the server side system 4002 via the network 4008. The server side system 4002 can process the search query 4012b and related information, and as shown by process arrows 4022 and 4032, search results may be sent to the client side system 4010b via the network 4008. Upon receipt, a set of search results 4016b may be presented to a user via the results interface 4018b.

As shown in this example, in some instances, the information retrieval system 4000 may initially provide similar query results (e.g., 4016a, 4016b) based on similar search queries (e.g., 4012a, 4012b). For example, multiple search result categories (e.g., Association football or soccer, Gridiron or American football, etc.) may be relevant to a search query (e.g., "football"), based on global search data and statistics. However, a user associated with one or more identified dimensions may be determined to generally prefer a particular search result or search result category. For example, for the search query "football", a user located in the United States may prefer search results that pertain to American football, and a user located in England may prefer search results that pertain to Association football (soccer). In this example, the user of client side system 4010a may be identified as being associated with a dimension 4050 (e.g., a location in the United States). The user of client side system 4010a in this example may interact with the search results 4016a (e.g., by selecting a particular result, by viewing information associated with the selected result for a certain amount of time, by scrolling through the results, by proceeding to another set of search results, etc.). For example, the user of client side system 4010a may select a query result link related to American football. As shown by process arrows 4028 and 4022, data related to the interaction, in addition to information associated with the identified dimension 4050 (e.g., a location in the United States), may be sent to the server side system 4002 via the network 4008. Additionally, in this example, the user of client side system 4010b may be associated with a dimension 4060 (e.g., a location in England). The user of client side system 4010b in this example may interact with the search results 4016b. For example, the user of client side system 4010b may select a query link related to Association football (soccer). As shown by process arrows 4034 and 4022, data related to the interaction, in addition to information associated with the identified dimension 4060 (e.g., a location in England), may be sent to the server side system 4002 via the network 4008.

One or more techniques may be implemented to associate an identified user dimension with preferred search results. For example, the information retrieval system 4000 may track preferred search results for search requestors (e.g., users) relative to one or more dimensions associated with the search requestors to produce one or more metrics. Upon the metric reaching a defined value, for example, one or more preferred search results may be determined for a search query provided by a search requestor associated with an identified dimension. For example, as shown by process arrow 4024, server side system 4002 may store information related to a search result preference (e.g., a preference for American football) based on a search query (e.g., search query 4012a, "football") provided by a search requestor (e.g., the user of client side system 4010a) associated with an identified dimension (e.g., dimension 4050, a location in the United States). Correspondingly, the server side system 4002 may store information related to a search result preference (e.g., a preference for Association football) based on a search query (e.g., search query 4012b, "football") provided by a search requestor (e.g., the user of client side system 4010b) associated with another identified dimension (e.g., dimension 4060, a location in England). Metrics (e.g., counts, percentages, weightings, etc.) may be produced (and maintained) for the identified dimensions, provided search queries, and preferred search results. For example, a count may be maintained for search results (e.g., results related to American football) preferred by search requestors associated with an identified dimension (e.g., a location in the United States) for a particular search query (e.g., "football"). Similar counts may be maintained for search results (e.g., results related to Association football) preferred by search requestors associated with other dimensions (e.g., a location in England). As such, multiple metrics may be produced (and maintained) for multiple identified dimensions, multiple search queries, and multiple search results, for example.

From the collected information from search requestors (e.g., search queries), dimensions, etc., the ranking of results for later submitted queries may be accordingly adjusted. For example, previously submitted queries, identified dimensions, etc. that reflect one or multiple characteristics of a search requestor may be used to adjust rankings. Referring to the figure, a user of client side system 4010c may provide a search query 4012c (e.g., "football") via the query interface 4014c, which, similar to the user of client side system 4010a, may reflect the location of the user. Also similar to client side system 4010a, client side system 4010c may be associated with one or more dimensions such as the dimension 4050 (e.g., a location in the United States). As shown by process arrows 4040 and 4022, the search query 4012c and dimensional information (e.g., information associated with dimension 4050) may be sent to the server side system 4002 via the network 4008. The server side system 4002 can process the search query 4012c and related information, for example by using one or more software modules (e.g., a search engine) executed by the server 4004. For example, an accentuator included in the search engine may identify one or more dimensions associated with the user of the client side system 4010c (e.g., dimension 4050, a location in the United States) and may adjust the ranking of search results based on metrics (e.g., counts, percentages, weightings, etc.)

associated with the identified dimensions, provided search queries, preferred search results, etc. In this example, information associated with the metrics may be retrievable from the data store 4006 for use by one or more software modules (e.g., the accentuator 1058, shown in FIG. 1) to adjust the search results rankings.

While one dimension may be used for adjusting query results, in some arrangements, multiple dimensions may be utilized for ranking results. Further, assigning priorities, weighting, and other techniques and methodologies may be used to distinguish and enhance one (or more) dimensions from another dimension (or multiple dimensions). For example, in some implementations, metrics associated with the language of a user may be given a higher priority compared to metrics associated with the location of a user. Similarly, temporal characteristics may be used as factors for adjusting query results. For example, in some implementations, query results associated with more recent information may be assigned a higher priority or assigned more weight than query results associated with less recent information. As shown by process arrows 4022 and 4042, in this example, adjusted search results may be sent to the client side system 4010c via the network 4008. Upon receipt, search results 4016c may be presented to the user via the results interface 4018c. Search results may be adjusted and presented in a manner which accentuates results determined to be relevant to users. For example, search results that reflect one or more dimensions of the users may be considered more relevant. Continuing with this particular example, the search results 4016c may be adjusted such that the ranking of results pertaining to American football are generally increased and the ranking of results pertaining to other types of football are generally decreased or in some instances, actively suppressed.

Similar to client side system 4010b, a user of client side system 4010d may provide a search query 4012d (e.g., "football") via the query interface 4014d. Also similar to client side system 4010b, the client side system 4010d or the user may be associated with dimension 4060 (e.g., a location in England). As shown by process arrows 4044 and 4022, the search query 4012d and dimensional information (e.g., information associated with dimension 4060) may be sent to the server side system 4002 for processing by using one or more software modules (e.g., a search engine). For example, an accentuator included in a search engine may identify one or more dimensions associated with the user of the client side system 4010d (e.g., dimension 4060, a location in England). Upon identifying the dimension(s), the accentuator may adjust the ranking of search results, e.g., based on metrics associated with previously identified dimensions, provided search queries, and preferred search results. For example, the information retrieval system 4000 may determine that a predetermined number of search requesters associated with the identified dimension (e.g., dimension 4060) submitted a similar search query (e.g., "football") and have shown a preference for a particular type of search result (e.g., results pertaining to Association football or soccer). Information reflective of this preference (e.g., metrics) may be stored (e.g., in data store 4006) for retrieving by server 4004 for use by one or more software modules (e.g., the accentuator 1058, shown in FIG. 1) for adjusting search result rankings. As shown by process arrows 4022 and 4046, adjusted search results may be sent to the client side system 4010d and presented to the user via the results interface 4018d. In this example, the ranking of the search results 4016d may be adjusted such that results pertaining to Association football (soccer) are accentuated and the ranking of results pertaining to other types of football are generally decreased or suppressed.

Figure 5:
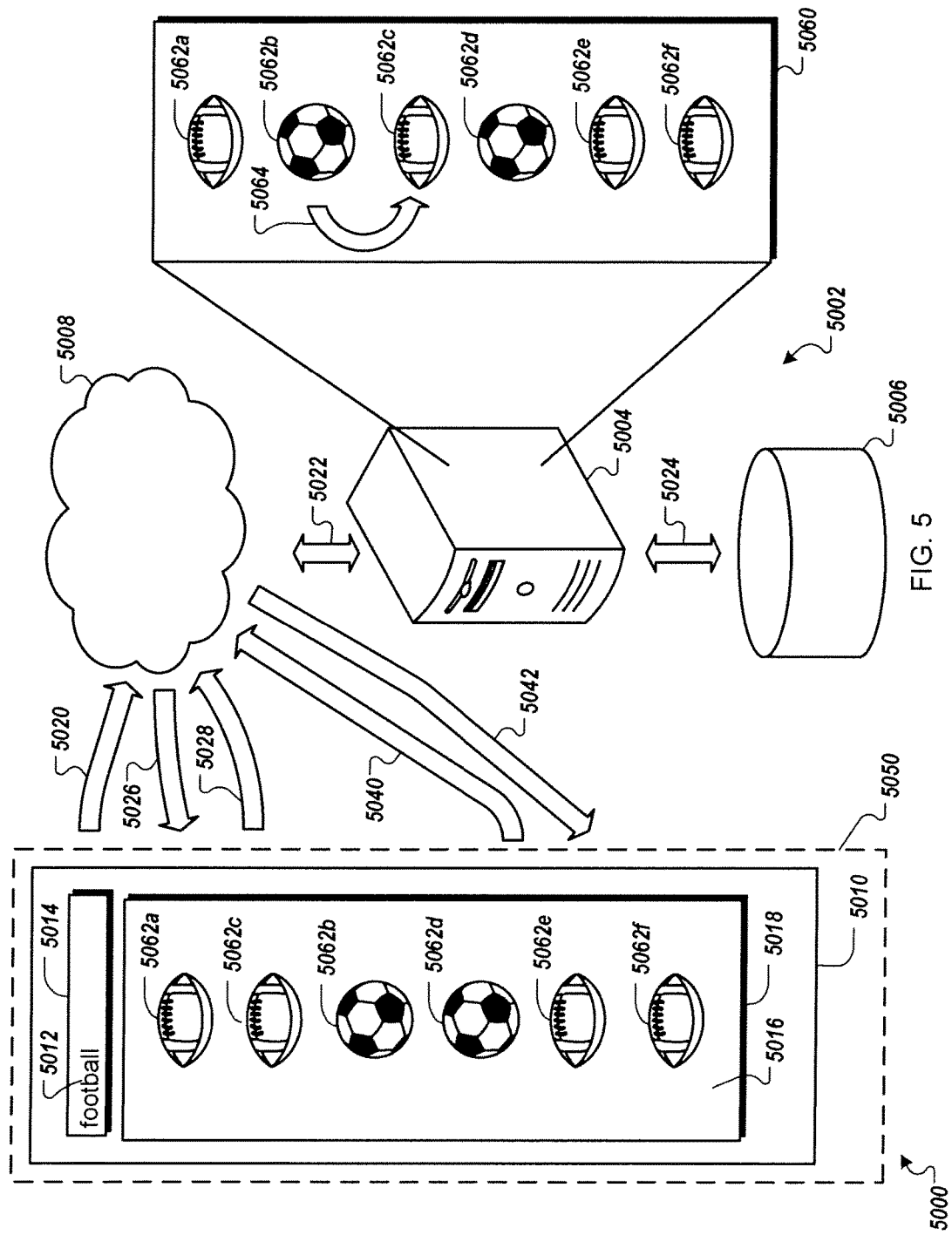
FIG. 5 illustrates an information retrieval search session.

Referring to FIG. 5, operations of an exemplary search session of an information retrieval system 5000 are illustrated. Similar to the systems shown in FIGS. 1, 2, 3, and 4 the information retrieval system 5000 can provide relevant results for search queries. For example, similar to client device 1004 (shown in FIG. 1), client side system 5010 can enable a user to enter search queries and interact with search results. Also, similar to server system 1014, a server side system 5002 can process search queries and generate search results that are correspondingly provided to any of the client side systems 5010. Being scalable, more or fewer client side systems and server side systems may be included in the information retrieval system 5000.

The client side system 5010 may include a query interface 5014 enabling a user to provide search queries. The client side system 5010 may also include a results interface 5018 that enables a user to view and interact with query results. Query results content may be provided in various types of representations; for example, such content may be provided in links, media, individually or in combination.

In order to retrieve search results, a user may enter a query into the query interface 5014, in this example, a query 5012 (e.g. "football"). As shown by process arrows 5020 and 5022, the search query 5012 and other information associated with a user (e.g. location, language, etc.) may be sent to the server side system 5002 via the network 5008. The server side system 5002 can process the search query 5012 and related information, for example by using one or more software modules (e.g., a search engine) executed by the server 5004. As shown by process arrow 5024, data (e.g. index information, dimensional information, search session statistics, etc.) may be retrieved from or stored in the data store 5006 and can be used by the server 5004 for providing a set of initial query results 5060. Data store 5006 is representative of various types of information sources that may be in communication with the server 5004. For example, one or more storage devices (e.g., hard drives, etc.), servers, and computing device equipment may be directly or indirectly (e.g., via one or more networks) in communication with the server 5004.

Each of the individual query results 5062a-f is associated with a score which is used to rank the result. The score of the individual results 5062a-f may be based on various factors. The score may be based on the number of times the query occurs in the document, where the query occurs in the document, the number of times the document has been selected by previous users entering the same or similar queries. For example, if previous users submit the query "football" and select "the NFL" search result, then "the NFL" is likely a good search result for later "football" queries. In some arrangements, a similar query may also result in an increased score, for example, if the previous user enters a query of "American football." The score may be further based on information known about the user such as the user's language, geographic location, demographic information and recent search history. For example, a user who enters an English language query is likely to be more interested in English language search results. English search results may also be preferred in an English speaking country. In this case, otherwise identical resources typically receive a higher score if they are in English. These different factors are combined to create a single score.

In some arrangements, each factor of a score for a search result 5062a-f may be associated with a trustworthiness factor or score which provides a measure of the reliability of the score. For example, one query result 5062*b* may have a relatively high score but a relatively low level of trustworthiness may be associated with that score, while another query result 5062*c* may have a lower score but a higher confidence level. Initially the initial query results 5060 may be sorted based on the score of the individual query results 5062*a-f*. Once the trustworthiness of the score is taken into account, the scores may be adjusted and the ranking may change.

In some arrangements, the trustworthiness of a factor may be considered as a measurement of confidence that applying the factor is likely to improve the search results for the user. For example, trustworthiness may be considered a measure of how likely results associated with a previous and similar query (e.g. "American Football" or "Futbol") may also provide good results for the current query (e.g. "football). In some arrangements, the similarity between current and previous queries may be measured using a similarity score.

In another example, trustworthiness may be considered a measure associated with the origins a document (or other type of search result). A searcher located in the United States may have results returned that originate from the United States, other English speaking countries, or anywhere in the world. Generally, results from the same country are more likely to satisfy the user than results from other countries that share a common language (e.g., other English speaking countries) or results from the rest of the world. Scores may be adjusted commensurately.

In another example, the trustworthiness of a factor may depend upon similarities shared among previous users and current users, e.g., based upon demographic information. Demographic information may include age, gender, race, income, education, computer type, browser type, employment status, location, and other similar factors. Each of these factors may produce their own individual measure or score of trustworthiness, which may or may not be further processed (e.g., aggregated). For example, search result selections of a previous user who is thirty-six years of age may be more likely to produce good results for a search initiated by a person thirty-four years of age than for a six year old individual.

Initially, the individual query results 5062*a-f* are scored individually and independently using several different criteria. Each criterion has a trustworthiness score associated with it; however, because the results are scored independent of one another the trustworthiness scores lack relative meaning. Therefore, the initial scores are made without regard to the trustworthiness associated with each of the criterion that contribute to the results. The results may be sorted based on the initial score. Once the query results 5060 are determined, the trustworthiness scores for each criterion are analyzed. Trustworthiness scores may be narrowly distributed, indicating an equal confidence in each score or trustworthiness scores may be widely distributed, indicating that scores from some criterion may be more reliable than other scores from the same criterion. The degree of distribution of trustworthiness scores may be determined using traditional methods. For example, the trustworthiness scores may be analyzed to determine a mean and a standard distribution of the score. In some arrangements, the standard distribution may be normalized. In general, a set of documents having a larger standard deviation of trustworthiness scores indicates a larger variation in the reliability of the scores. Similarly, a small standard deviation indicates that the trustworthiness of each score is similar. In some arrangements, the trustworthiness scores may be considered highly distributed if the difference between the most trustworthiness and the least trustworthy scores exceeds a threshold. In other arrangements, the distribution of the trustworthiness scores may be based on the number of intervals in the distribution, for example the number of binomial confidence intervals. In other arrangements, the distribution of scores may be considered highly distributed based on the shape of the distribution curve, for example, a distribution curve which contains multiple peaks may be considered widely distributed, similarly a distribution curve with a long tail may be considered widely distributed. If the trustworthiness of the results is sufficiently distributed, that is there are items with relatively high trustworthiness and other items with relatively low trustworthiness, the portion of the result score associated with the criterion may be compared and adjusted. In a similar manner, the score may be modified to reflect the relative trustworthiness of multiple criteria. In this example, as represented by process arrow 5064, the individual query result 5062*b* may have its score reduced to reflect the relative lack of confidence in criteria contributing to the score when compared to the other query results 5062*a, c-f*. As shown by process arrows 5022 and 5042, in this example, adjusted search results may be sent to the client side system 5010 via the network 5008. Upon receipt, search results 5016 containing the individual search results 5062*a-f* may be presented to the user via the results interface 5018. The search results may be presented in a manner which reflects the adjustments made on the server. In this example, individual query result 5062*b* has been demoted and is presented in a less relevant position than query result 5062*c*.

Figure 6:
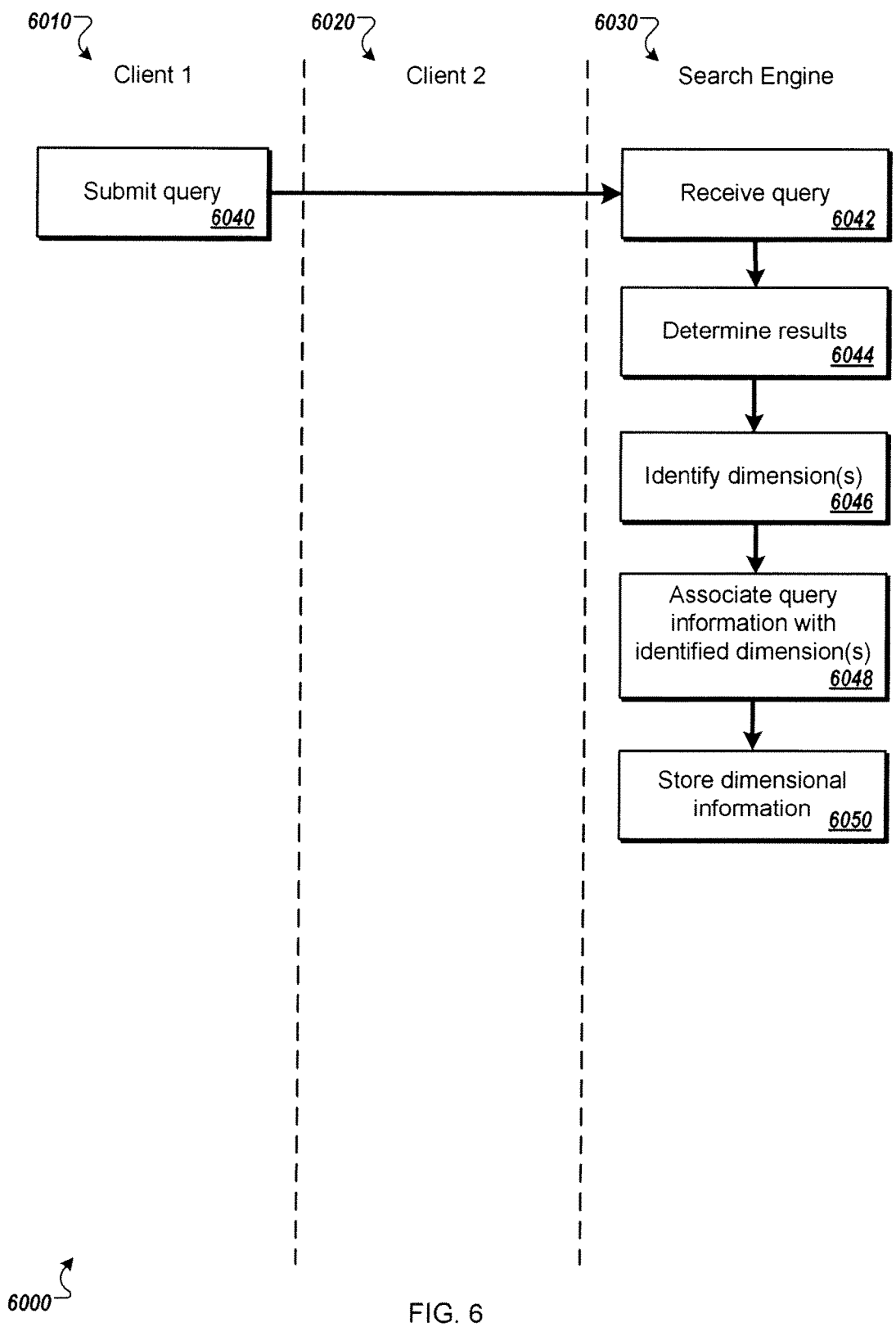
FIG. 6 is diagram illustrating an identification of dimensional information from search queries.
Figure 7:
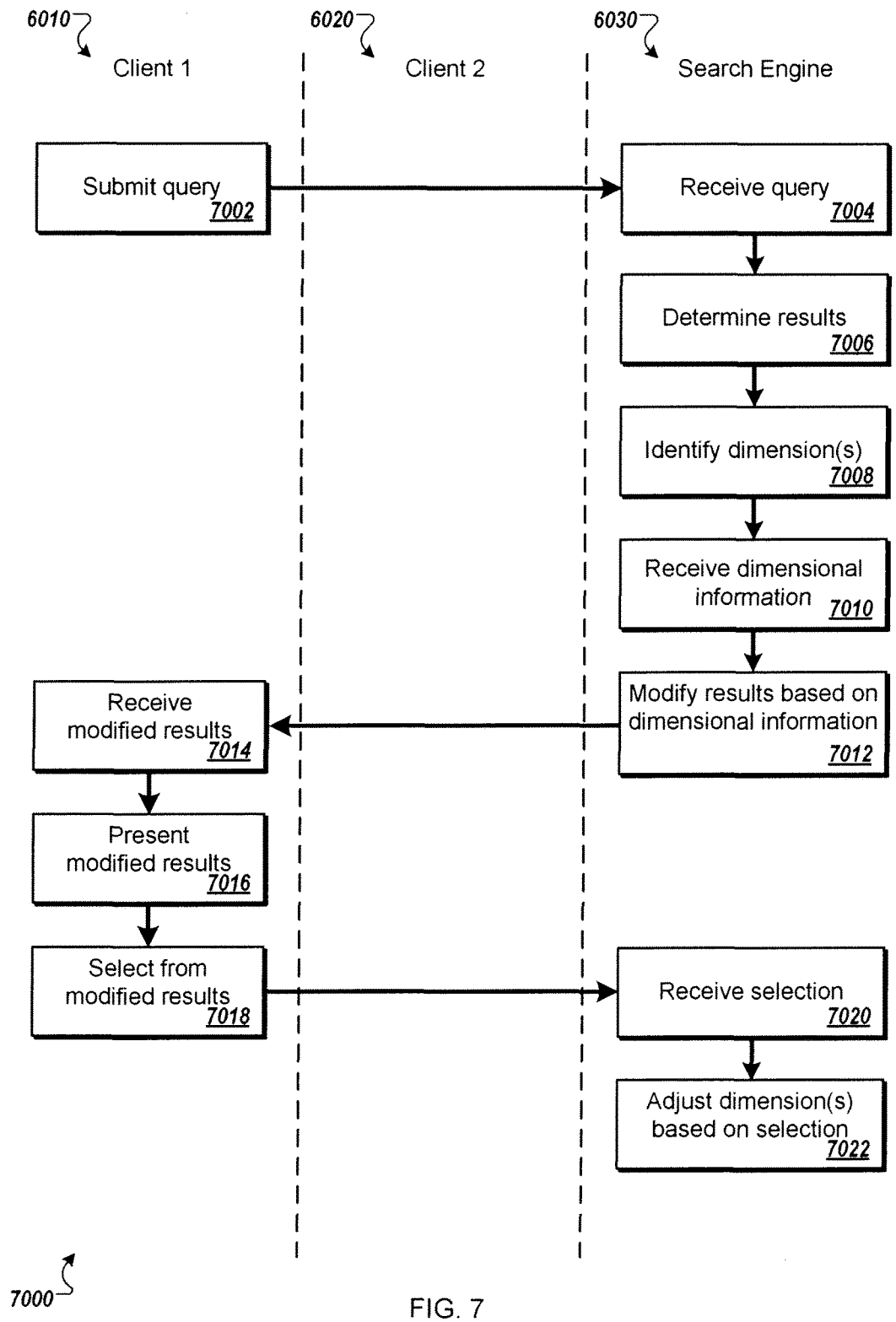
FIG. 7 is diagram illustrating an adjustment of search rankings and dimensional information.
Figure 8:
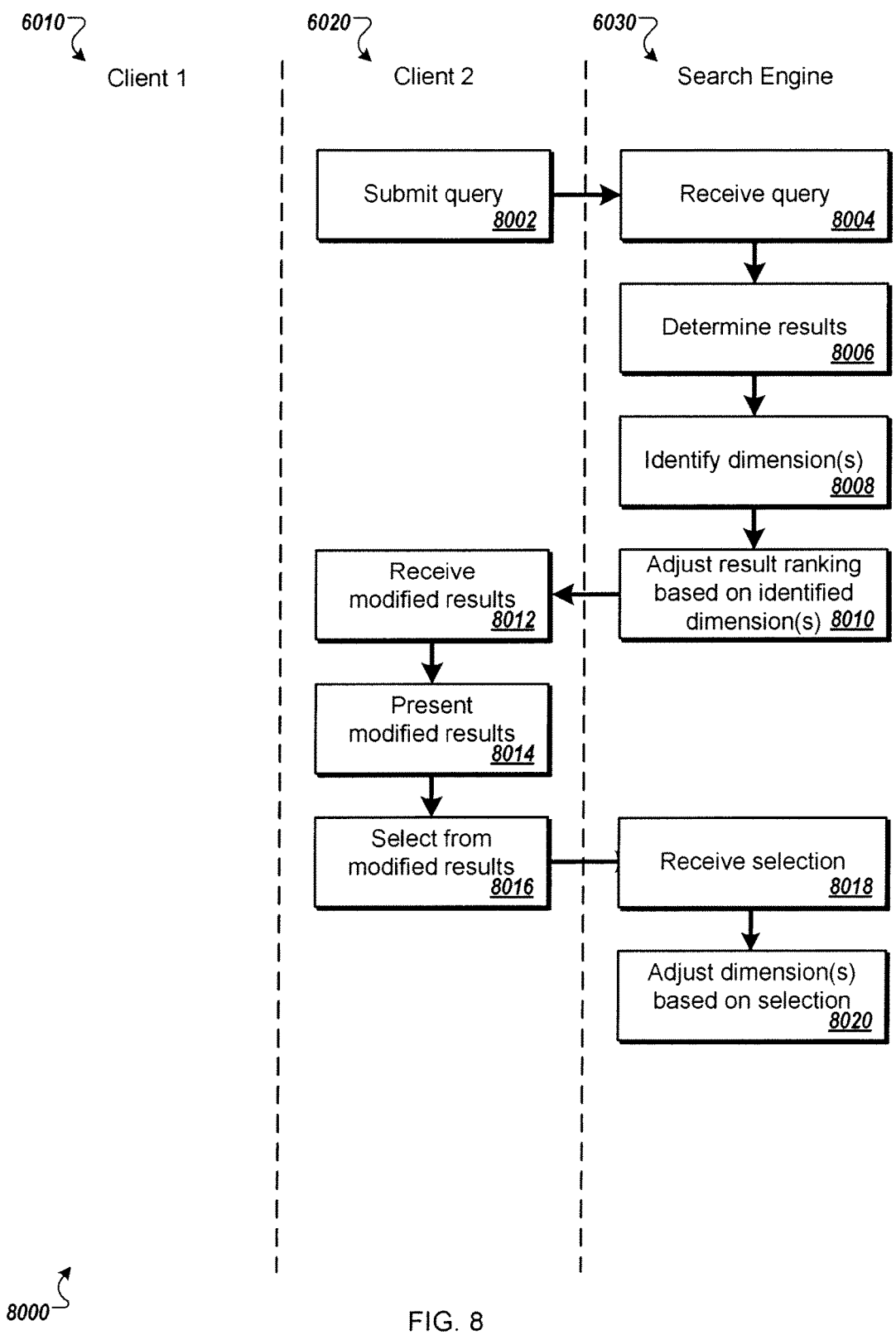
FIG. 8 is diagram illustrating a further adjustment of search rankings and dimensional information.

Referring to FIGS. 6-8, interactions are illustrated among multiple clients 6010 and 6020 and a search engine 6030 that includes an accentuator (such as the accentuator 2080 shown in FIG. 2). For example, clients 6010 and 6020 may represent clients similar to clients 1004*a-c* (shown in FIG. 1). Similarly, operations of the search engine 6030 may be similar to operations of search engine 1030 (also shown in FIG. 1).

For purposes of illustration, search sessions for two clients are shown, however, any number of search sessions may be conducted by any number of clients (e.g., three or more clients). In some arrangements, a user may conduct an initial search session from one client and may conduct a subsequent search session from the same client or from another client. Interactions among the search engine 6030 and clients (e.g., clients 6010, 6020, etc.) may be concurrently executed. For example, the search engine 6030 may perform search operations (e.g., receiving search queries, determining matches (search results), identifying one or more dimensions, storing and retrieving data, etc.) for one client while also performing operations related to one or more other clients.

Referring to FIG. 6, a diagram 6000 illustrates identifying dimensional information from search queries. Such operations may be initiated by client 6010 submitting 6040 query that is provided to the search engine 6030. Along with the query, additional information may also be provided to the search engine 6030, for example, temporal information (e.g., time of day, day of week, month or season of year, proximity to events such as sporting competitions and elections, etc.) may be provided by a search requestor or client device in association with the search query. Such temporal information may be used to define or identify dimensional information associated with a user. For example, the gender of a user could be determined from the types of searches executed at a particular time of the day or evening. Selected search results may also factor into dimension identification. For example, search result selections, frequency of selection, changing selections with time, etc. may be used. Operations of the search engine 6030 may include receiving 6042 the search query and determining 6044 results related to the provided query. In some arrangements, the results may include a ranked listing of search results based on the search query (e.g., provided by the client 6010). From the query provided, and potentially other collected information (e.g., previous search queries, result selections, etc.), operations of the search engine 6030 may include identifying 6046 one or more dimensions associated with the client 6010 (e.g., a user), associating 6048 query information with the identified dimensions (e.g., determining a relationship between a search query and a user characteristic), and storing 6050 dimensional information (e.g., in index database 1022, shown in FIG. 1). As shown in this example, dimensional information may be identified, associated with query information, and stored based upon provided queries and other user or client information.

Referring to FIG. 7, a diagram 7000 illustrates adjusting search rankings and dimensional information. For example, based upon identified dimensional information, the ranking of search results may be adjusted. Similarly, dimensional information may be adjusted, for example, based upon search results, user selections and other types of information. To illustrate such adjustments, initial operations of the client 6010 may include submitting 7002 a query to the search engine 6030. Along with the query, additional information may be provided for assisting in search result identification and ranking. For example, temporal information and dimensional information (e.g., information related to a search requestor's location, language, demographics, personal traits, areas of interest, etc.) may be provided by the client 6010, retrieved from storage (e.g., index database 1022, shown in FIG. 1). Similar to the operations described in FIG. 5, exemplary operations of the search engine 6030 may include receiving 7004 the query and determining 7006 search results. For example, search results may include a tabulated listing that is ranked based on the search query provided by the client 6010. Using dimensional information, the search results may be adjusted to accentuate results that may be more highly associated with the client 6010 than other search results. To provide such an adjustment, operations of the search engine 6030 may include identifying 7008 one or more dimensions of the client 6010. For example, the dimensions may be identified using information related to provided search queries (e.g., language, spelling, topics, etc.), dimensional information provided by a search requestor or client device, temporal information, along with other information. Once received 7010, the dimensional information may be used to modify 7012 the search results. For example, one or more software modules associated with the search engine 6030 (e.g., the accentuator 1058, shown in FIG. 1) may provide operations to adjust the search result rankings. The software module(s), for example, may remove, decrease the rank, increase the rank of one or more search results, or perform a combination of ranking adjustments. Once received 7014, the client 6010 presents 7016 the modified search results, for example, on a display device associated with the client 6010. Further operations of the client 6010 include enabling a user of the device to select 7018 from the modified results. For example, a user may interact with the search results and may indicate a preference for a particular search result (e.g., by clicking a link associated with the search result, accessing information associated with the search result, dwelling on a search result, etc.). Further operations of the search engine 6030 include receiving 7020 the selection (e.g., a preference) and adjusting 7022 one or more dimensions based on the selection. As shown in this example, interactions of the user with the search results (e.g., selections, viewing time, other types of click data, etc.) may be used to adjust dimensional information. For example, one or more metrics may be maintained by the search engine 6030 to enable the engine to refine processes for identifying dimensions and to refine processes for modifying query results based on dimensional information.

Referring to FIG. 8, a diagram 8000 illustrates further adjusting search rankings and dimensional information. For example, based on previously identified dimensional information provided by one or more clients associated with one or more similar dimensions, the client 6020 may receive a set of query results particularly relevant to a submitted query. Based on further query result interactions provided by the client 6020, for example, the identified dimensions may be further refined. Exemplary operations of the client 6020 include submitting 8002 a query to the search engine 6030. Additionally, the client 6020 may provide temporal and dimensional information, for example. Exemplary operations of the search engine 6030 include receiving 8004 the query and determining 8006 results. For example, the results may include a ranked listing of search results based on the search query provided by the client 6020. Further operations of the search engine 6030 include identifying 8008 one or more dimensions associated with a user of the client 6020. For example, the dimensions may be identified using information related to provided search queries, dimensional information provided by a search requestor or client device, and provided temporal information. In some implementations, one or more dimensions may be associated with the recency of data indicative of search requestor behavior relative to previously submitted queries. For example, search results more recently preferred by users associated with one or more similar dimensions (e.g., a user of the client 6010) may be given additional weight or value as compared to search results preferred less recently. Further operations of the search engine 6030 include adjusting 8010 result ranking based on the identified dimensions. For example, one or more software modules associated with the search engine 6030 (e.g., the accentuator 1058, shown in FIG. 1) may adjust the search result rankings. Further operations of the client 6020 include receiving 8012 and presenting 8014 (e.g., on a display device) the modified search results. Further operations of the client 6020 include enabling a user of the device to select 8016 from the modified results. Further operations of the search engine 6030 include receiving 8018 the selection (e.g., a preference) and adjusting 8020 one or more dimensions based on the selection.

Figure 9:
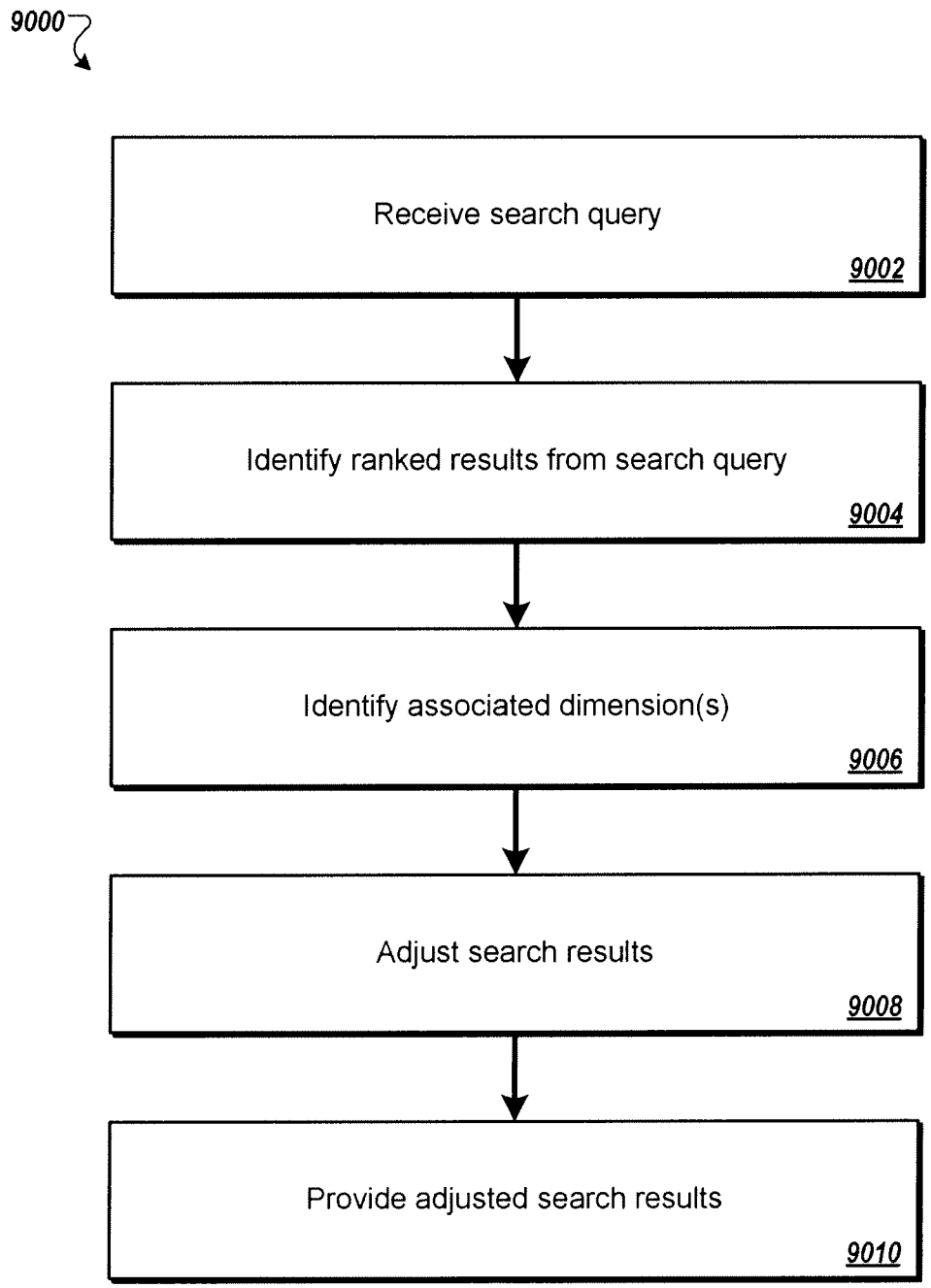
FIG. 9 shows a flowchart that represents operations of an accentuator.

Referring to FIG. 9, a flowchart 9000 represents some operations of an accentuator (such as the accentuator 1058 shown in FIG. 1). The operations may be executed by a single computing device (such as the server system 1014 shown in FIG. 1) that includes a search engine. In some arrangements, multiple computing devices may also be utilized. Along with being executed at a single site (e.g., server system 1014), operation execution may be distributed among two or more sites (e.g., server system 1014 and client 1004).

Among other capabilities, the accentuator 1058 may use search query data and identify one or more dimensions representative of characteristics (e.g., location, language, demographics, personal traits, etc.) associated with the search requestor. To provide this functionality, the accentuator 1058 may execute operations such as receiving 9002 data representative of one or more search queries. Search query data, for example, may be included in one or more search sessions conducted by a search requestor (e.g., a client user). Various types of data may be associated with a search session, for example, data related to search queries, user characteristics, click data, and the like. Upon receiving the search query data, operations may also include identifying 9004 ranked results from the search query. For example, the results may be identified and individually scored and ranked by an accentuator (e.g., the accentuator 1058 as shown in FIG. 1).

Operations of the accentuator 1058 may also include identifying 9006 one or more associated dimensions. The dimensions may be representative of at least one characteristic associated with the search requestor associated with the search session. For example, the dimensions may be associated with a requestor location, a user language, a user demographic (e.g., gender, age, etc.), a user trait (e.g., profession, level of education, etc.), etc. The dimensions, for example, may also be associated with or derived from one or more user interactions (e.g., click data, etc.). For example, click data from previous search queries initiated by the requestor may represent user preferences and behavior that may be used for dimension identification. Characteristics of the collected data may also be utilized, for example, the particular time that data is collected may factor into identifying one or dimensions. For example, more recent search requestor behavior may receive greater weight or higher preference for identifying or using user dimensions. Similarly, in another example, more recent search results may receive greater weight or higher preference.

Upon identifying one or more user dimensions, operations may also include adjusting 9008 search results, for example, by using the identified dimensions. The adjustment, for example, may be indicative of search requestor behavior relative to previously submitted queries. In some implementations, search results adjustments may be based on one or more combinations of user dimensions. For example, two dimensions may be identified by a requestor in which one dimension may be associated with the language of the search requestor and another dimension may be associated with the geographical location of the requestor. Priorities or weights may be assigned to any of the dimensions. For example, one of the dimensions may be assigned a priority or a higher weight relative to one or more other dimensions (e.g., assigning language a higher weight as compared with location, etc.). The priorities or weights may be used for performing a search result ranking adjustment based on a combination of dimensions. Upon adjusting search results, operations may also include providing 9010 the adjusted search results. For example, the search results may be provided to a client device (e.g., client 1004a, shown in FIG. 1) used by a search requestor.

Figure 10:
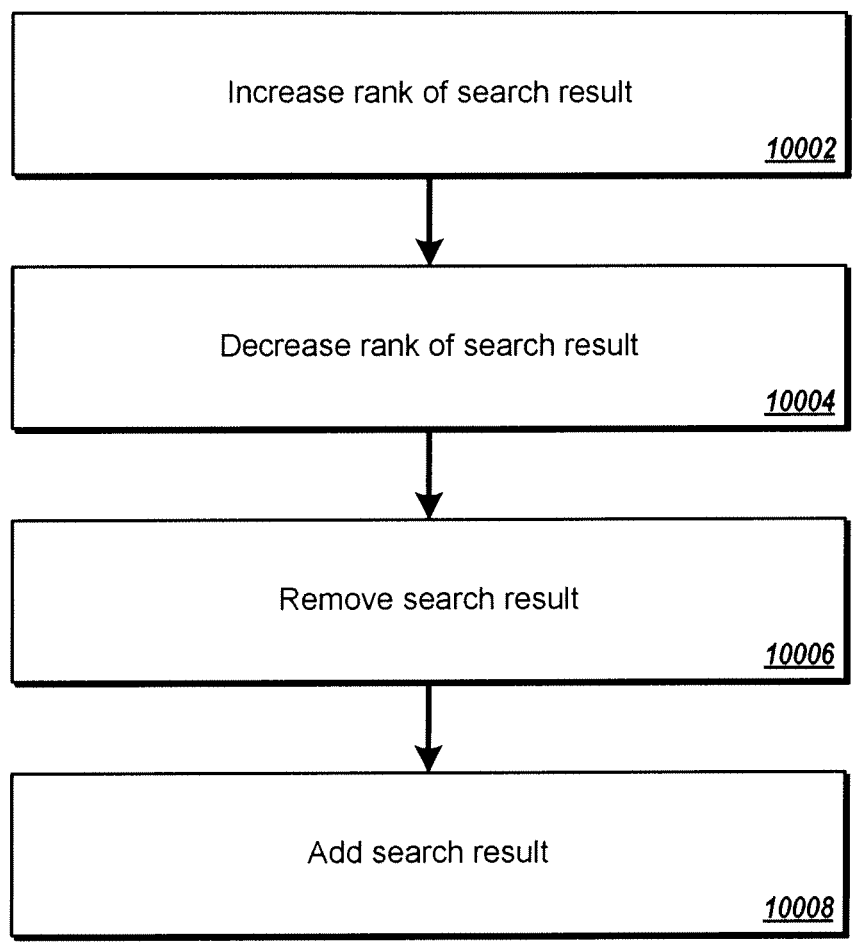
FIG. 10 shows a chart that represents operations of an accentuator.

Referring to FIG. 10, a chart 10000 represents some additional operations of an accentuator (such as the accentuator 1058 shown in FIG. 1). The operations may be executed by a single computing device (such as the server system 1014 shown in FIG. 1) that includes a search engine. In some arrangements, multiple computing devices may also be utilized. Along with being executed at a single site (e.g., server system 1014), operation execution may be distributed among two or more sites (e.g., server system 1014 and client 1004).

As described in the flowchart 9000 (shown in FIG. 9), one operation of the accentuator may include adjusting 9008 search results. Such adjustments may be based upon information provided by one or more dimensions. To provide such adjustment capabilities, various types of operations may be provided. For example, operations may include increasing 10002 the rank of one or more search results. As another example, operations may include decreasing 10004 the rank of one or more search results. For a set of individually scored and ranked search results, the accentuator 1058 may increase or decrease the rank of a particular result based on an availability of result ranking data associated with a user dimension, for example. If such ranking data is available, for example, a specific ranking (e.g., a ranking based on local data) may receive preference over a general ranking (e.g., a ranking based on global data). For example, the ranking of documents determined to be more relevant to users associated with one or more common dimensions may be generally increased and the ranking of document determined to be less relevant to users associated with one or more common dimensions may be generally decreased. Adjustments may be applied using a variety of methods (e.g., by applying multipliers, priorities, etc.). In one arrangement, the accentuator 1058 may determine a distribution of trustworthiness scores and reduce a document's score based on its relative position within the distribution. For example, a document with a relatively low trustworthiness score, as compared to the other documents, would have its score decreased by a large amount. Similarly, a document with a high trustworthiness score may not have its score adjusted at all. The adjusted document scores and used to adjust the relative position of the documents within the ranking.

Operations of the accentuator 1058 may also include removing 10006 one or more search results, for example. As another example, operations may include adding 10008 one or more search results. For example, for a set of individually scored and ranked search results, the accentuator 1058 may remove or add particular search results based on the availability of result ranking data associated with a user dimension. For example, rankings based on global data may be blocked or filtered. Additionally, rankings based on results preference data (e.g., click data, etc.) associated with users identified with one or more common dimensions may be used in place of global ranking data.

Figure 11:
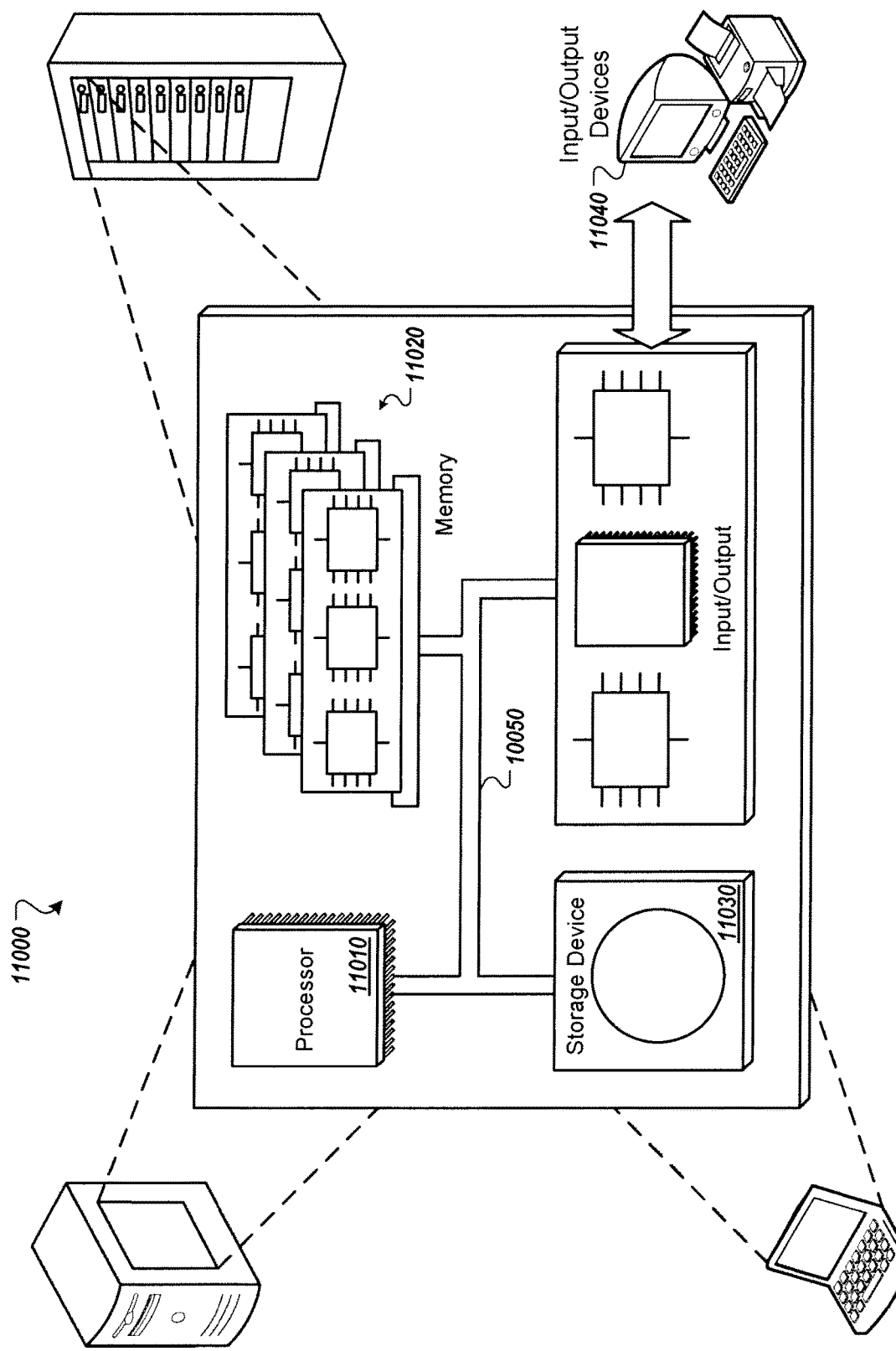
FIG. 11 shows a schematic diagram of an example computer system.

FIG. 11 is a schematic diagram of an example computer system 11000. The system 11000 can be used for practicing operations described above. The system 11000 can include a processor 11010, a memory 11020, a storage device 11030, and input/output devices 11040. Each of the components 11010, 11020, 11030, and 11040 are interconnected using a system bus 11050. The processor 11010 is capable of processing instructions within the system 11000. These instructions can implement one or more aspects of the systems, components and techniques described above. In some implementations, the processor 11010 is a single-threaded processor. In other implementations, the processor 11010 is a multi-threaded processor. The processor 11010 can include multiple processing cores and is capable of processing instructions stored in the memory 11020 or on the storage device 11030 to display graphical information for a user interface on the input/output device 11040.

The memory 11020 is a computer readable medium such as volatile or non volatile that stores information within the system 11000. The memory 11020 can store processes related to the functionality of the search engine 1030 (shown in FIG. 1), for example. The storage device 11030 is capable of providing persistent storage for the system 11000. The storage device 11030 can include a floppy disk device, a hard disk device, an optical disk device, or a tape device, or other suitable persistent storage mediums. The storage device 11030 can store the various databases described above. The input/output device 11040 provides input/output operations for the system 11000. The input/output device 11040 can include a keyboard, a pointing device, and a display unit for displaying graphical user interfaces.

The computer system shown in FIG. 11 is but one example. In general, embodiments of the subject matter and the functional operations described in this specification can be implemented in digital electronic circuitry, or in computer software, firmware, or hardware, including the structures disclosed in this specification and their structural equivalents, or in combinations of one or more of them. Embodiments of the subject matter described in this specification can be implemented as one or more computer program products, i.e., one or more modules of computer program instructions encoded on a computer readable medium for execution by, or to control the operation of, data processing apparatus. The computer readable medium can be a machine-readable storage device, a machine-readable storage substrate, a memory device, a composition of matter effecting a machine-readable propagated signal, or a combination of one or more of them. The term "data processing apparatus" encompasses all apparatus, devices, and machines for processing data, including by way of example a programmable processor, a computer, or multiple processors or computers. The apparatus can include, in addition to hardware, code that creates an execution environment for the computer program in question, e.g., code that constitutes processor firmware, a protocol stack, a database management system, an operating system, or a combination of one or more of them. A propagated signal is an artificially generated signal, e.g., a machine-generated electrical, optical, or electromagnetic signal, that is generated to encode information for transmission to suitable receiver apparatus.

A computer program (also known as a program, software, software application, script, or code) can be written in any form of programming language, including compiled or interpreted languages, and it can be deployed in any form, including as a stand alone program or as a module, component, subroutine, or other unit suitable for use in a computing environment. A computer program does not necessarily correspond to a file in a file system. A program can be stored in a portion of a file that holds other programs or data (e.g., one or more scripts stored in a markup language document), in a single file dedicated to the program in question, or in multiple coordinated files (e.g., files that store one or more modules, sub programs, or portions of code). A computer program can be deployed to be executed on one computer or on multiple computers that are located at one site or distributed across multiple sites and interconnected by a communication network.

The processes and logic flows described in this specification can be performed by one or more programmable processors executing one or more computer programs to perform functions by operating on input data and generating output. The processes and logic flows can also be performed by, and apparatus can also be implemented as, special purpose logic circuitry, e.g., an FPGA (field programmable gate array) or an ASIC (application specific integrated circuit).

Processors suitable for the execution of a computer program include, by way of example, both general and special purpose microprocessors, and any one or more processors of any kind of digital computer. Generally, a processor will receive instructions and data from a read only memory or a random access memory or both. The essential elements of a computer are a processor for performing instructions and one or more memory devices for storing instructions and data. Generally, a computer will also include, or be operatively coupled to receive data from or transfer data to, or both, one or more mass storage devices for storing data, e.g., magnetic, magneto optical disks, or optical disks. However, a computer need not have such devices. Moreover, a computer can be embedded in another device, e.g., a mobile telephone, a personal digital assistant (PDA), a mobile audio player, a Global Positioning System (GPS) receiver, to name just a few. Computer readable media suitable for storing computer program instructions and data include all forms of non volatile memory, media and memory devices, including by way of example semiconductor memory devices, e.g., EPROM, EEPROM, and flash memory devices; magnetic disks, e.g., internal hard disks or removable disks; magneto optical disks; and CD ROM and DVD-ROM disks. The processor and the memory can be supplemented by, or incorporated in, special purpose logic circuitry.

To provide for interaction with a user, embodiments of the subject matter described in this specification can be implemented on a computer having a display device, e.g., a CRT (cathode ray tube) or LCD (liquid crystal display) monitor, for displaying information to the user and a keyboard and a pointing device, e.g., a mouse or a trackball, by which the user can provide input to the computer. Other kinds of devices can be used to provide for interaction with a user as well; for example, feedback provided to the user can be any form of sensory feedback, e.g., visual feedback, auditory feedback, or tactile feedback; and input from the user can be received in any form, including acoustic, speech, or tactile input.

Embodiments of the invention can be implemented in a computing system that includes a back-end component, e.g., as a data server, or that includes a middleware component, e.g., an application server, or that includes a front-end component, e.g., a client computer having a graphical user interface or a Web browser through which a user can interact with an implementation of the invention, or any combination of one or more such back-end, middleware, or front-end components. The components of the system can be interconnected by any form or medium of digital data communication, e.g., a communication network. Examples of communication networks include a local area network ("LAN") and a wide area network ("WAN"), e.g., the Internet.

The computing system can include clients and servers. A client and server are generally remote from each other and typically interact through a communication network. The relationship of client and server arises by virtue of computer programs running on the respective computers and having a client-server relationship to each other.

While this specification contains many specifics, these should not be construed as limitations on the scope of the invention or of what may be claimed, but rather as descriptions of features specific to particular embodiments of the invention. Certain features that are described in this specification in the context of separate embodiments can also be implemented in combination in a single embodiment. Conversely, various features that are described in the context of a single embodiment can also be implemented in multiple embodiments separately or in any suitable subcombination. Moreover, although features may be described above as acting in certain combinations and even initially claimed as such, one or more features from a claimed combination can in some cases be excised from the combination, and the claimed combination may be directed to a subcombination or variation of a subcombination.

Similarly, while operations are depicted in the drawings in a particular order, this should not be understood as requiring that such operations be performed in the particular order shown or in sequential order, or that all illustrated operations be performed, to achieve desirable results. In certain circumstances, multitasking and parallel processing may be advantageous. Moreover, the separation of various system components in the embodiments described above should not be understood as requiring such separation in all embodiments, and it should be understood that the described program components and systems can generally be integrated together in a single software product or packaged into multiple software products.

Thus, particular embodiments of the invention have been described. Other embodiments are within the scope of the following claims. For example, the actions recited in the claims can be performed in a different order and still achieve desirable results. Moreover, the server environment, which is configured to provide electronic search service and employ the ranking systems and techniques described, need not be implemented using traditional back-end or middleware components. The server environment can be implemented using a program installed on a personal computing apparatus and used for electronic search of local files, or the server environment can be implemented using a search appliance installed in an enterprise network.

Other implicit user feedback models can be used in place of the traditional click fraction model described. For example, an implicit user feedback model employing a large-scale logistic regression model that uses the actual query and url as features can be used. The new prior models can be used to denormalize any query-specific click model.

In addition, the prior model(s) can be applied in varying manners. For example, a prior model can be applied at run time as an adjustment to the ranking boost given to a document in accordance with the implicit user feedback model since the set of features used for the prior model can be available for direct input at run time. Alternatively, the prior model can be applied at model building time, where features are fetched from the log(s), which can result in improved response time during searches. In addition, when the model is applied at building time, the implicit feedback can be adjusted per each click record before aggregating the feedback from multiple clicks into a signal. This adjustment can be for instance a weighting of the clicks according to how much they were affected by display bias before the clicks are aggregated. At run time, the signal is typically only adjusted after the clicks were already aggregated, which can result in some loss of precision.

What is claimed is:

1. A computer-implemented method, comprising:
receiving documents responsive to a query, each document having a respective associated score indicative of the document's relevance to the query, wherein:
each respective associated score is based on a respective value for each of a plurality of different score factors;
each score factor for a given associated score corresponds to a different criterion than each other score factor for the given associated score; and
each score factor has a respective trustworthiness score that indicates a respective reliability of values determined based on the score factor;
determining, based on the trustworthiness scores for the score factors of a plurality of the associated scores of a plurality of different documents, a value-based distribution of the trustworthiness scores for each of the different score factors of the plurality of associated scores along a dimension based on relative values of the trustworthiness scores, the distribution including trustworthiness scores for multiple score factors for each of the different documents;
adjusting the value of at least one score factor of a given associated score by an amount that is determined based on:
a relative position of the at least one score factor's respective trustworthiness score in the distribution with respect to other trustworthiness scores in the distribution; and
a measure of how widely the trustworthiness scores for each of the different score factors of the plurality of associated scores are distributed in the distribution;
adjusting the given associated score based on the adjusted value of the at least one score factor; and
ranking the documents to account for the adjusted associated score.

2. The method of claim 1, wherein the distribution is a frequency distribution and wherein the amount is determined based on a distance between a lowest and a highest trustworthiness score in the distribution and the at least one score factor's trustworthiness score.

3. The method of claim 1, wherein the amount is determined based on a number of intervals in the distribution and the at least one score factor's trustworthiness score.

4. The method of claim 1, wherein the amount is determined based on a shape of the distribution and the score factor's trustworthiness score.

5. The method of claim 1, wherein a first score factor of the plurality of score factors of a particular associated score represents an amount added to an information retrieval score for the document associated with the particular associated score.

6. The method of claim 1, further comprising providing the ranked documents to a client.

7. The method of claim 1, wherein each score factor's trustworthiness score is determined by a metric that calculates a degree of trustworthiness for the score factor.

8. The method of claim 1, wherein the trustworthiness score of a particular score factor is based on a language of the score factor's associated document.

9. The method of claim 1, wherein the trustworthiness score of a particular score factor is based on a similarity between the query and a previous query.

10. The method of claim 1, wherein the trustworthiness score of a particular score factor is based on a country from which the query was submitted and a country in which the documents were created.

11. A computer program product, encoded on a machine-readable storage device, operable to cause a data processing apparatus to perform operations comprising:
receiving documents responsive to a query, each document having a respective associated score indicative of the document's relevance to the query, wherein:
each respective associated score is based on a respective value for each of a plurality of different score factors;
each score factor for a given associated score corresponds to a different criterion than each other score factor for the given associated score; and
each score factor has a respective trustworthiness score that indicates a respective reliability of values determined based on the score factor;
determining, based on the trustworthiness scores for the score factors of a plurality of the associated scores of a plurality of different documents, a value-based distribution of the trustworthiness scores for each of the different score factors of the plurality of associated scores along a dimension based on relative values of the trustworthiness scores, the distribution including trustworthiness scores for multiple score factors for each of the different documents;
adjusting the value of at least one score factor of a given associated score by an amount that is determined based on:
a relative position of the at least one score factor's respective trustworthiness score in the distribution with respect to other trustworthiness scores in the distribution; and
a measure of how widely the trustworthiness scores for each of the different score factors of the plurality of associated scores are distributed in the distribution;
adjusting the given associated score based on the adjusted value of the at least one score factor; and
ranking the documents to account for the adjusted associated score.

12. The computer program product of claim 11, wherein the distribution is a frequency distribution and wherein the amount is determined based on a distance between a lowest and a highest trustworthiness score in the distribution and the at least one score factor's trustworthiness score.

13. The computer program product of claim 11, wherein the amount is determined based on a number of intervals in the distribution and the at least one score factor's trustworthiness score.

14. The computer program product of claim 11, wherein the amount is determined based on a shape of the distribution and the score factor's trustworthiness score.

15. The computer program product of claim 11, wherein a first score factor of the plurality of score factors of a particular associated score represents an amount added to an information retrieval score for the document associated with the particular associated score.

16. The computer program product of claim 11, wherein the operations further comprise providing the ranked documents to a client.

17. The computer program product of claim 11, wherein each score factor's trustworthiness score is determined by a metric that calculates a degree of trustworthiness for the score factor.

18. The computer program product of claim 11, wherein the trustworthiness score of a particular score factor is based on a language of the score factor's associated document.

19. The computer program product of claim 11, wherein the trustworthiness score of a particular score factor is based on a similarity between the query and a previous query.

20. The computer program product of claim 11, wherein the trustworthiness score of a particular score factor is based on a country from which the query was submitted and a country in which the documents were created.

21. A system for processing search results, comprising:
one or more computers; and
a computer-readable medium coupled to the one or more computers having instructions stored thereon which, when executed by the one or more computers, cause the one or more computers to perform operations comprising:
receiving documents responsive to a query, each document having a respective associated score indicative of the document's relevance to the query, wherein:
each respective associated score is based on a plurality of different score factors;
each score factor for a given associated score corresponds to a different criterion than each other score factor for the given associated score; and
each score factor has a respective trustworthiness score that indicates a respective reliability of values determined based on the score factor;
determining, based on the trustworthiness scores for the score factors of a plurality of the associated scores of a plurality of different documents, a value-based distribution of the trustworthiness scores for each of the different score factors of the plurality of associated scores along a dimension based on relative values of the trustworthiness scores, the distribution including trustworthiness scores for multiple score factors for each of the different documents;
adjusting the value of at least one score factor of a given associated score by an amount that is determined based on:
a relative position of the at least one score factor's respective trustworthiness score in the distribution with respect to other trustworthiness scores in the distribution; and
a measure of how widely the trustworthiness scores for each of the different score factors of the plurality of associated scores are distributed in the distribution;
adjusting the given associated score based on the adjusted value of the at least one score factor; and
ranking the documents to account for the adjusted score.

22. The system of claim 21, wherein the distribution is a frequency distribution and wherein the amount is determined based on a distance between a lowest and a highest trustworthiness score in the distribution and the at least one score factor's trustworthiness score.

23. The system of claim 21, wherein the amount is determined based on a number of intervals in the distribution and the at least one score factor's trustworthiness score.

24. The system of claim 21, wherein the amount is determined based on a shape of the distribution and the score factor's trustworthiness score.

25. The system of claim 21, wherein a first score factor of the plurality of score factors of a particular associated score represents an amount added to an information retrieval score for the document associated with the particular associated score.

26. The system of claim 21, wherein the operations further comprise providing the ranked documents to a client.

27. The system of claim 21, wherein each score factor's trustworthiness score is determined by a metric that calculates a degree of trustworthiness for the score factor.

28. The system of claim 21, wherein the trustworthiness score of a particular score factor is based on a language of the score factor's associated document.

29. The system of claim 21, wherein the trustworthiness score of a particular score factor is based on a similarity between the query and a previous query.

30. The system of claim 21, wherein the trustworthiness score of a particular score factor is based on a country from which the query was submitted and a country in which the documents were created.

31. The method of claim 1, further comprising:
determining that the measure of how widely the trustworthiness scores for each of the different score factors of the plurality of associated scores are distributed in the distribution satisfies a threshold; and adjusting the value of the at least one score factor of a given associated score whenever the measure of how widely the trustworthiness scores for each of the different score factors of the plurality of associated scores are distributed in the distribution satisfies the threshold.

32. The method of claim 1, wherein the respective trustworthiness score for each score factor is a measure of confidence that the score factor is likely to improve search results provided to a user that submitted the query.

* * * * *